(12) United States Patent
Shibasaki et al.

(10) Patent No.: US 10,335,098 B2
(45) Date of Patent: Jul. 2, 2019

(54) PANORAMIC IMAGING APPARATUS AND DIAGNOSTIC IMAGING METHOD IN SAME APPARATUS

(71) Applicant: AXION JAPAN CO., LTD., Saitama (JP)

(72) Inventors: Yuki Shibasaki, Tokyo (JP); Hideo Sakurai, Tokyo (JP); Motoyuki Kawamura, Tokyo (JP); Kazuo Harai, Tokyo (JP); Masato Minabe, Chiba (JP); Takashi Sue, Tokyo (JP)

(73) Assignee: AXION JAPAN CO., LTD., Saitama (JP)

( * ) Notice: Subject to any disclaimer, the term of this patent is extended or adjusted under 35 U.S.C. 154(b) by 67 days.

(21) Appl. No.: 14/901,195

(22) PCT Filed: Jul. 17, 2014

(86) PCT No.: PCT/JP2014/003804
§ 371 (c)(1),
(2) Date: Dec. 28, 2015

(87) PCT Pub. No.: WO2015/008491
PCT Pub. Date: Jan. 22, 2015

(65) Prior Publication Data
US 2016/0151026 A1 Jun. 2, 2016

(30) Foreign Application Priority Data

Jul. 19, 2013 (JP) .................................. 2013-162741

(51) Int. Cl.
*A61B 6/00* (2006.01)
*A61B 6/03* (2006.01)
(Continued)

(52) U.S. Cl.
CPC ................ *A61B 6/14* (2013.01); *A61B 6/461* (2013.01); *A61B 6/463* (2013.01); *A61B 6/465* (2013.01);
(Continued)

(58) Field of Classification Search
CPC .. A61B 6/00; A61B 6/02; A61B 6/025; A61B 6/027; A61B 6/14; A61B 6/42;
(Continued)

(56) References Cited

U.S. PATENT DOCUMENTS 7,488,109 B2 * 2/2009 Hangartner .......... A61B 6/4035
378/168
8,417,010 B1 * 4/2013 Colby ...................... A61B 6/14
378/168
(Continued)

FOREIGN PATENT DOCUMENTS

JP  11-047095    2/1999
JP  2001-061873  3/2001
(Continued)

*Primary Examiner* — Anastasia Midkiff
(74) *Attorney, Agent, or Firm* — Clark & Brody

(57) ABSTRACT

In a panoramic imaging apparatus, a panoramic image is displayed on a monitor. The panoramic image is an image in which an overall dentition is in optimal focus, or an image in which a region of interest that is a portion of the image of the overall dentition is in optimal focus. Both images are reconstructed from frame data that has been collected by an initial first scan. Feature points of one or more teeth and a supporting portion that supports the tooth in the dentition in the panoramic image displayed on the monitor are designated. A length based on the positions of the designated feature points is measured in the panoramic image. The degree of loss in alveolar bone that supports the tooth is (Continued)

analyzed based on the measured length. The analysis information is provided to a dentist as check information regarding periodontal disease.

15 Claims, 16 Drawing Sheets

(51) Int. Cl.
*A61B 6/14* (2006.01)
*G06T 7/00* (2017.01)
*G06T 7/33* (2017.01)
*A61C 19/04* (2006.01)
*H04N 5/232* (2006.01)

(52) U.S. Cl.
CPC .............. *A61B 6/469* (2013.01); *A61B 6/505* (2013.01); *A61B 6/5217* (2013.01); *A61B 6/5223* (2013.01); *A61B 6/5294* (2013.01); *A61C 19/041* (2013.01); *A61C 19/042* (2013.01); *A61C 19/043* (2013.01); *G06T 7/0016* (2013.01); *G06T 7/33* (2017.01); *A61B 6/032* (2013.01); *A61B 6/467* (2013.01); *A61B 6/5205* (2013.01); *G06T 7/0012* (2013.01); *G06T 7/0014* (2013.01); *G06T 7/97* (2017.01); *G06T 2200/24* (2013.01); *G06T 2207/10072* (2013.01); *G06T 2207/10124* (2013.01); *G06T 2207/20096* (2013.01); *G06T 2207/20101* (2013.01); *G06T 2207/20104* (2013.01); *G06T 2207/30008* (2013.01); *G06T 2207/30036* (2013.01); *H04N 5/23238* (2013.01)

(58) Field of Classification Search
CPC ........... A61B 6/46; A61B 6/461; A61B 6/463; A61B 6/465–469; A61B 6/48; A61B 6/50; A61B 6/201; A61B 6/505; A61B 6/52; A61B 6/5211; A61B 6/5217; A61B 6/5223; A61B 6/5229; A61B 6/5235; A61B 6/5294; A61B 5/00; A61B 5/0059; A61B 5/0062; A61B 5/0082; A61B 5/0088; A61B 5/103; A61B 5/107; A61B 5/1072; A61B 5/1075; A61B 5/1076; A61B 5/1178; A61B 5/45; A61B 5/4504; A61B 5/4538; A61B 5/4542; A61B 5/4547; A61B 5/4552; A61B 5/4557; A61B 5/4842; A61B 5/7275; A61B 5/74; A61B 5/742; A61B 5/7425; A61B 5/743; A61B 5/7435; G06T 7/00; G06T 7/0002; G06T 7/0012; G06T 7/0014; G06T 7/0016; G06T 7/30; G06T 7/32; G06T 7/33; G06T 7/337; G06T 7/344; G06T 7/38; G06T 7/50; G06T 7/55; G06T 7/60; G06T 7/62; G06T 7/70; G06T 7/73; G06T 7/74; G06T 7/75; G06T 7/97; G06T 2207/00; G06T 2207/10; G06T 2207/10072; G06T 2207/10081; G06T 2207/10116; G06T 2207/10124; G06T 2207/20; G06T 2207/20068; G06T 2207/20092; G06T 2207/20096; G06T 2207/20101; G06T 2207/20104; G06T 2207/20108; G06T 2207/30; G06T 2207/30004; G06T 2207/30008; G06T 2207/30036; G06F 19/00; G06F 19/30; G06F 19/32; G06F 19/34; G06F 19/3437; G06F 19/3487; G03B 37/00; G03B 37/005; G03B 37/02; G03B 42/00; G03B 42/02; G03B 42/026; H04N 5/23238; A61C 19/00; A61C 19/04; A61C 19/041; A61C 19/042; A61C 19/043

See application file for complete search history.

(56) References Cited

U.S. PATENT DOCUMENTS

| | | | |
|---|---|---|---|
| 2011/0036360 A1* | 2/2011 | Lang | A61B 6/505 128/898 |
| 2013/0108011 A1* | 5/2013 | Sadakane | A61B 6/03 378/19 |
| 2013/0286174 A1* | 10/2013 | Urakabe | A61B 1/00009 348/66 |
| 2014/1234796 | 8/2014 | Tsuji et al. | |
| 2014/0314776 A1* | 10/2014 | Ke | C07K 16/22 424/139.1 |

FOREIGN PATENT DOCUMENTS

| | | |
|---|---|---|
| JP | 2001-333898 | 12/2001 |
| JP | 2007-136163 | 6/2007 |
| JP | 2009-226016 | 10/2009 |
| JP | 2011-098047 | 5/2011 |

* cited by examiner

FIG.12
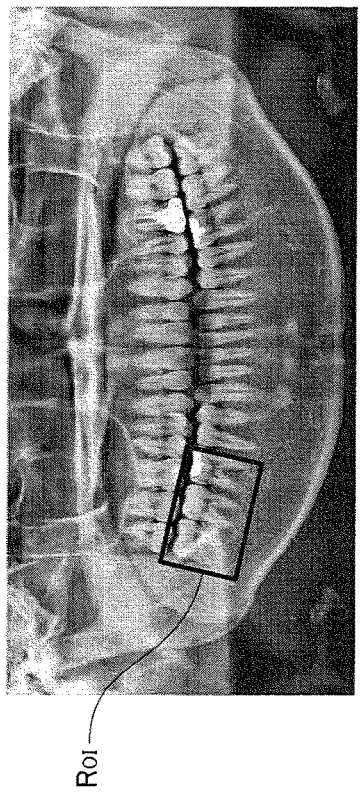
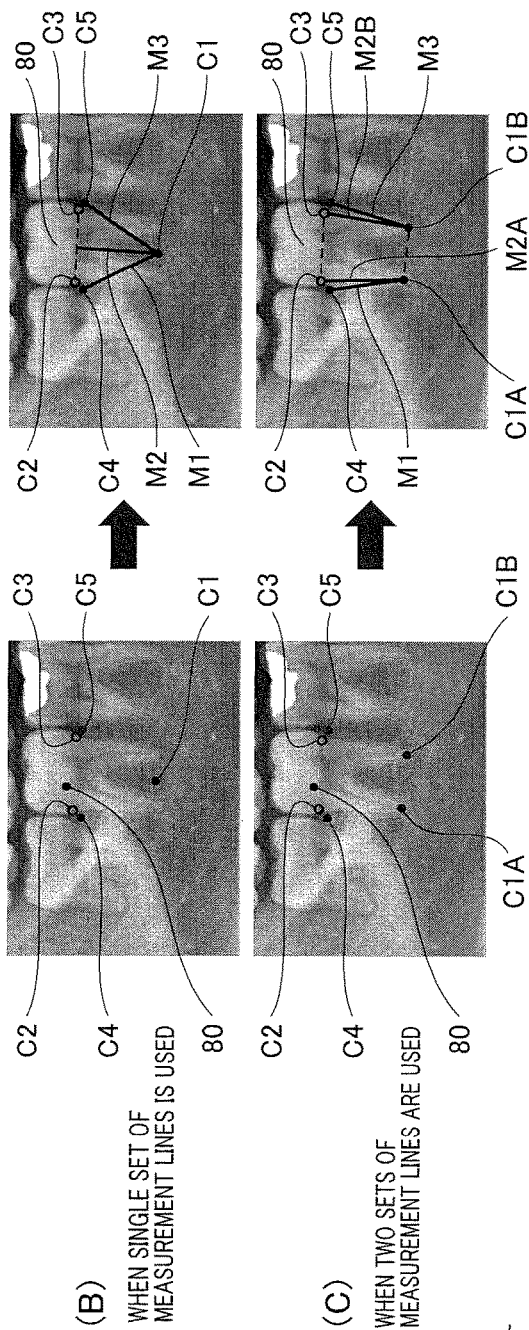

PANORAMIC IMAGING APPARATUS AND DIAGNOSTIC IMAGING METHOD IN SAME APPARATUS

CROSS-REFERENCE TO RELATED APPLICATION

This application is based on and claims the benefit of priority from earlier Japanese Patent Application No. 2013-162741 filed Jul. 19, 2013 the description of which are incorporated herein by reference.

TECHNICAL FIELD

The present invention relates to an apparatus and a method for examining the state of progression of periodontal disease in a subject (patient). In particular, the present invention relates to an apparatus and a method for examining the state of progression of periodontal disease from data of a panoramic image of a jaw portion of a subject captured based on a tomosynthesis method in which X-rays are used.

BACKGROUND ART

With the changes in dietary culture and lifestyles over the recent years, an increasingly large number of people are receiving dental treatment. Dental experts often warn of the necessity of regular checkups and early treatment of teeth. When dental treatment is performed, in many cases, roentgenography for examining the state of teeth (dentition) and gums is performed. Conventionally, roentgenography mostly involves acquisition of a localized projection image of a gum area using X-ray film. As an alternative method to roentgenography or a method concomitantly used therewith, an X-ray computed tomography (CT) scanner, a dental panoramic imaging apparatus dedicated to dentistry, or the like is used.

The X-ray CT scanner merely applies a typical CT imaging method to the imaging of the jaw portion. The resolution of a panoramic image along the dentition that has been reconstructed from images acquired by the scanner is not very high. The X-ray CT scanner is limited for use in examination of the overall dentition.

Meanwhile, in the dental panoramic imaging apparatus, an X-ray source and X-ray detector pair is positioned so as to sandwich the jaw portion of a subject therebetween. The pair is then moved around the jaw portion, and radiolucency data is collected. A panoramic image along a predetermined cross-section in relation to the dentition is generated from the collected data. The dental panoramic imaging apparatus includes an analog-type panoramic imaging apparatus that uses film and developers, and a digital-type panoramic imaging apparatus that uses an imaging plate, such as a charge-coupled device (CCD) or a complementary metal-oxide-semiconductor (CMOS).

A typical digital-type panoramic imaging apparatus is provided with a revolution driving means. The revolution driving means integrally revolves an X-ray source and an X-ray image detecting unit around a subject. The X-ray source and the X-ray image detecting unit are disposed such as to oppose each other with the subject therebetween. The X-ray source includes an X-ray tube and a collimator that narrows the X-ray irradiated (or emitted) from the X-ray tube into a split-beam state. The X-ray image detecting unit includes an X-ray detector, such as an X-ray CCD or CMOS sensor. The X-ray detector outputs an electrical signal in digital quantity that is based on an incident X-ray quantity. Furthermore, the panoramic imaging apparatus includes a storage means and an image processing means. The storage means successively stores therein image information collected by the X-ray detector as frame images. The image processing means successively reads out the image information from the storage means at a predetermined time interval. The image processing means adds the pieces of image information that have been read out, while shifting each piece of image information by a predetermined distance, in relation to the direction in which an image moves over the continuous pieces of image information. The image processing means thereby forms a panoramic image of an arbitrary cross-section, based on the read-out interval and the amount of shifting of the pieces of image information. This image formation method is also referred to as a tomosynthesis method. As a result, a panoramic image of a cross-section along the dentition of a patient can be provided as an image for diagnosis on a monitor, such as a personal computer, without the use of X-ray films.

Meanwhile, periodontal disease refers to disease that occurs in the periphery of the teeth, that is, the gingiva, alveolar bone, periodontal membrane, or the cementum portion under the surface of the tooth root. However, in general, periodontal disease refers to an inflammatory disease that occurs around a tooth and is caused by bacteria, such as porphyromonas gingivalis. More than 90 percent of patients have this type of periodontal disease. Therefore, the present invention, described hereafter, also primarily targets the typical type of periodontal disease. The typical type of periodontal disease is referred to, hereafter, as "periodontal disease" and is differentiated from other types of periodontal disease.

To start treatment of periodontal disease, first, an examination is conducted to discover the current state of symptoms, that is, the extent of progression of the symptoms. A diagnosis is then made regarding the symptoms that will result. Various methods have been developed up to now. The primary examination methods today include a method that involves probing, an examination method in which dental X-rays are used, and an examination method in which microbial examination is used. Furthermore, when an examination is conducted, individual differences in the aspects of dental roots and alveolar bone, individual differences in dental bite, and the like also need to be considered.

The probing examination method is a method in which a probe (examination exploratory probe) is inserted into a pocket that is formed around a tooth. The state of symptoms is explored while measuring the depth of the pocket. The probing examination method is the simplest method and superior in terms of being applicable to all stages of symptoms. However, the examination results differ based on the skills of the technician, the anatomical aspects of the teeth, the attachment of tartar, and the like. In addition, when inflammation of the bottom portion of the periodontal pocket is severe, a problem occurs in that the probe damages the tissue in the bottom portion of the periodontal pocket and the patient experiences pain. That is, the depth of the pocket is measured by the probe (the probe for examination, and specifically, a calibrated probe referred to as a pocket probe) being inserted until the bottom portion of the pocket is reached. However, measurement is taken at about six sites for a single tooth and may be accompanied by bleeding. The examination causes the patient pain and is troublesome. Furthermore, even when the depth of the pocket is the same, the volume of the tooth below the pocket differs depending on the tooth and the individual. Therefore, the strength supporting the tooth cannot be determined by the depth of the tooth alone. A problem occurs in that the depth of the pocket is insufficient as an objective indicator of periodontal disease.

The examination method in which dental X-rays are used is a method in which bone level and outer shape of the alveolar bone are grasped from an X-ray photograph of a tooth and periodontal tissue, and examined. This method is superior to the probing method, in which measurement error is an issue, in that resorption of the alveolar bone and the outer shape of the alveolar bone can be accurately read. However, this method cannot be used at an early stage of periodontal disease and cannot be used often. In addition, in many cases, the dental X-ray images are unclear. A problem occurs in that accuracy may decrease.

The examination method in which microbial examination is used is a method in which the bacteria causing a periodontal infection is examined. The activity and progression of periodontal disease are examined. That is, the strength of pathogenicity is thought to differ depending on the bacteria strain. Disease activity is determined through identification of the bacteria strain. However, a problem occurs in that the identification of bacteria strain is time-consuming and costly, and the accuracy of prediction of disease activity (progression and recurrence of periodontal disease) is not very high.

CITATION LIST

Patent Literature

[PTL 2] JP-A-H11-047095
[PTL 3] JP-A-2011-98047

In response to such problems, a remaining teeth prediction system is proposed, as described in PTL 1. In the remaining teeth prediction system, the degree of reduction in total effective tooth root surface area is determined from the current total effective tooth root surface area. The degree of reduction in the number of remaining teeth is then predicted from the result. In this technique, the number of remaining teeth is predicted by output of a reduction curve or a reduction line of the total effective tooth root surface area.

In addition, an electronic medical auxiliary apparatus is proposed, as described in PTL 2. The electronic medical auxiliary apparatus compares a plaque score, the depth of a periodontal pocket, and the degree of vibration of a tooth with past data to calculate the degree of progression of periodontal disease. The electronic medical auxiliary apparatus then displays information indicating the predicted progression of periodontal disease based on the calculated degree of progression.

Furthermore, as described in PTL 3, an examination method is proposed in which volume rendering is performed on a plurality of dental X-ray CT images to acquire a three-dimensional image. Data on the tooth cervix, root apex, and alveolar bone crest are detected from the displayed three-dimensional image, and the state of progression of periodontal disease is detected.

SUMMARY OF INVENTION

Technical Problem

However, the techniques for grasping and presenting the state of progression of periodontal disease, described in above-described PTL 1 to 3, are confronted with unsolved issues.

Specifically, in the method for predicting the number of remaining teeth described in PTL 1, the tooth root surface area is calculated from an attachment level (the proportion of an area in which the gingiva is attached to the teeth) that is acquired by probing. Therefore, high prediction accuracy is difficult to achieve, in terms of the resorption of alveolar bone not being considered.

In addition, the prediction technique described in PTL 2 is not necessarily able to satisfactorily achieve prediction accuracy for the progression of periodontal disease, in terms of the resorption of alveolar bone not being considered.

Furthermore, the technique described in PTL 3 requires a dental X-ray CT apparatus, and therefore, apparatus installation cost is high. Typical dental clinics are not necessarily able to perform measurement. The technique cannot be considered a simple examination method.

The present invention has been achieved in light of the circumstances confronting the above-described conventional checking methods for periodontal disease. An object of the present invention is to provide an apparatus and a method that enable more highly accurate information regarding the occurrence or the state of progression of periodontal disease to be acquired and provided to a dentist.

Solution to Problem

To achieve the above-described object, according to an aspect of the present invention, there is provided a panoramic imaging apparatus characterized by including: an X-ray source that emits X-rays; a detector that converts the incident X-rays into electrical signals in digital quantity for each pixel and outputs the electrical signals as two-dimensional frame data at a fixed rate; a moving means for moving the X-ray source and the detector around a jaw portion of a subject, in a state in which the X-ray source and the detector oppose each other with the jaw portion therebetween; a storage means for storing the frame data outputted by the detector while the moving means is moving the X-ray source and the detector around the jaw portion; an image generating means for generating an optimally focused panoramic image of a cross-section along a dentition in the jaw portion, based on the frame data stored in the storage means; an image displaying means for displaying the panoramic image; a designating means for designating feature points of one or more teeth and a supporting portion that supports the tooth in the dentition and a reference point based on the feature points, in the panoramic image displayed in the display means; a measuring means for measuring, in the panoramic image, a length based on the positions of the feature points or reference point designated by the designating means; an analyzing means for analyzing the degree of loss in alveolar bone that supports the tooth, based on the length measured by the measuring means; and an analyzing means for analyzing the degree of loss in alveolar bone that supports the tooth, based on position information measured by the measuring means.

The feature points are, for example, a tooth cervix and a root apex of the tooth, and a crest of the alveolar bone.

According to another aspect, a diagnostic imaging method for a panoramic image having a similar configuration and a computer program capable of executing the method are also provided.

Effects of the Invention

In the present invention, as a result of a panoramic image merely being captured once through roentgenography along a horseshoe-shaped cross-section of the dentition of a subject, a panoramic image that is in optimal focus can be reconstructed based on the imaging data (frame data). In addition, checking for periodontal disease can be performed through use of the image. The panoramic image that is in optimal focus may be displayed. Feature points of a tooth and a support portion thereof may be designated on a screen on which the panoramic image is displayed. Information on the designated position may be measured, and the extent of loss in alveolar bone may be analyzed based on the measured position information. Through this simple technique, more highly accurate information based on the occurrence and degree of progression of periodontal disease can be provided to a dentist.

BRIEF DESCRIPTION OF DRAWINGS

In the accompanying drawings:

FIG. 12 is a diagram for explaining a method for setting measurement lines in first and second variation examples;

DESCRIPTION OF EMBODIMENTS

Modes (embodiments) for carrying out the present invention will hereinafter be described with reference to the accompanying drawings.

First Embodiment

First, a panoramic imaging apparatus according to a first embodiment of the present invention will be described with reference to FIG. 1 to FIG. 7.

The panoramic imaging apparatus has a function for acquiring a panoramic image based on a tomosynthesis method in which X-rays are used, and a function for providing information indicating the occurrence and state of progression of periodontal disease in the dentition (a row of teeth or a tooth row) in a jaw portion of a subject (such as a patient) from data of the panoramic image.

Configurations and operations of the panoramic imaging apparatus that are related to the acquisition of a panoramic image are identical to those in JP-A-2007-136163 (Patent Application No. 2006-284593; Patent No. 4844886) already published by the present applicants. Therefore, in the present application, descriptions of the configurations and operations related to the acquisition of a panoramic image are limited to overviews thereof. Meanwhile, the provision of information indicating the state of progression of periodontal disease will be described in detail.

[Configuration Related to Panoramic Image Acquisition Function]

First, an overview of a configuration related to a panoramic image acquisition function will be described.

Figure 1:
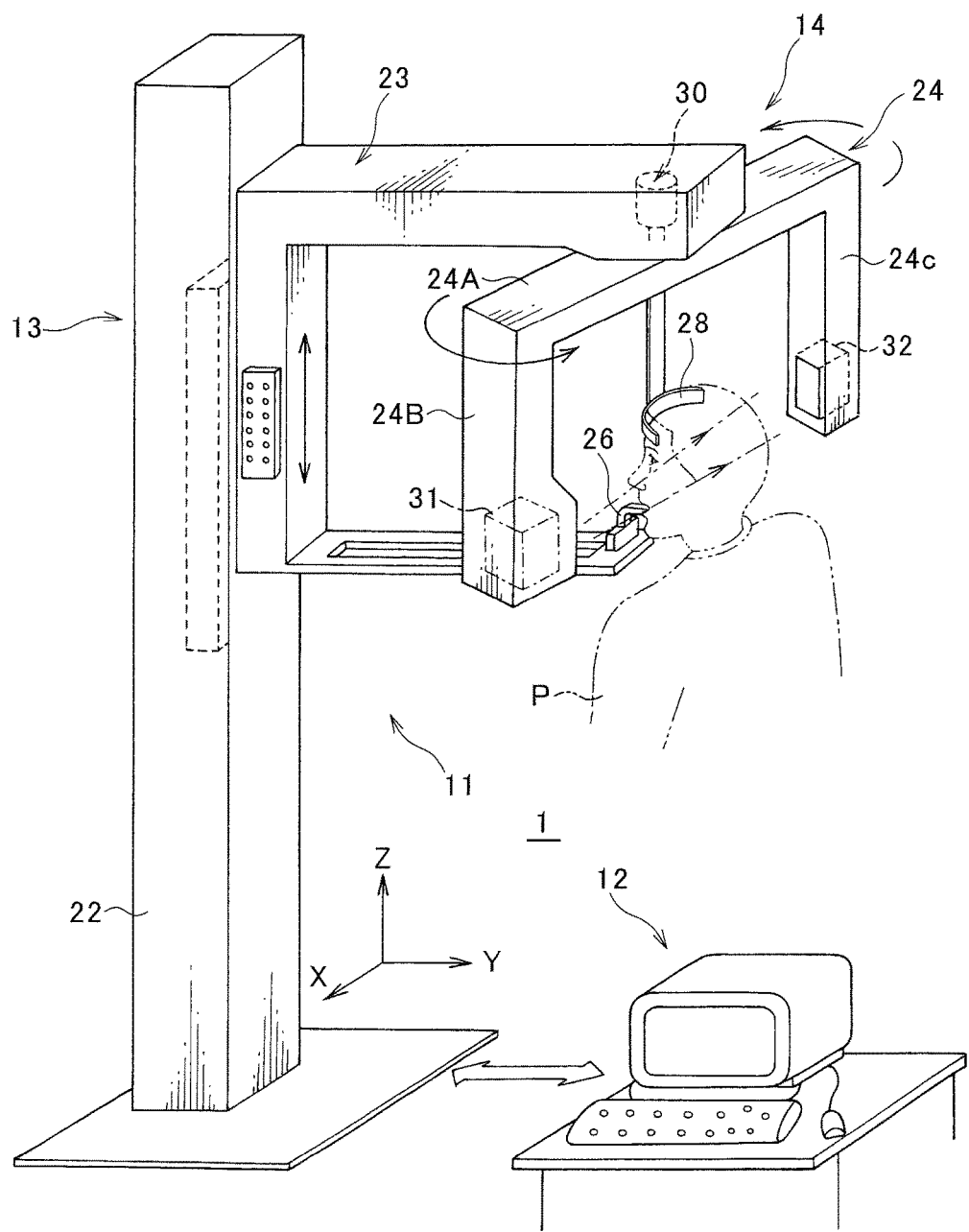
FIG. 1 is a perspective view for explaining an overview of a panoramic imaging apparatus according to a first embodiment of the present invention.

FIG. 1 shows an overview of a panoramic imaging apparatus 1 according to the present embodiment. As shown in FIG. 1, the panoramic imaging apparatus 1 includes a case 11 and a control and calculation apparatus 12. The case 11 collects gray-level, original image data for panoramic image generation from a subject (patient) who is in a standing position, for example. The control and calculation apparatus 12 is configured by a computer that controls data collection by the case 11, generates a panoramic image by loading the collected data, and performs post-processing of the panoramic image interactively with an operator (doctor or technician).

The case 11 includes a stand portion 13 and an imaging unit 14 that is capable of up/down movement in relation to the stand portion 13. For explanatory purposes, as shown in FIG. 1, an orthogonal coordinate system composed of X, Y, and Z axes is set with the long direction of the stand portion 13 as the Z axis.

The imaging unit 14 includes an up/down moving unit 23 and a rotating unit 24. The up/down moving unit 23 is substantially U-shaped when viewed from a side surface thereof. The rotating unit 24 is supported by the up/down moving unit 23 such as to be capable of rotating (turning). The up/down moving unit 23 is capable of moving in the Z-axis direction (vertical direction) over a predetermined range in the height direction, via a driving mechanism (not shown) that is set inside a support column portion 22.

The rotating unit 24 hangs down from the up/down moving unit 23 and rotates by being urged by drive from a rotation driving mechanism 30. The rotating unit 24 is substantially U-shaped when viewed from one side surface thereof, in a state of use. The rotating unit 24 is integrally provided with a lateral arm 24A, and left and right vertical arms (first vertical arm and second vertical arm) 24B and 24C. The lateral arm 24A rotates (turns) in a substantially parallel manner in a lateral direction, that is, within the XY plane. The left and right vertical arms 24B and 24C extend downward (Z-axis direction) from both end portions in the long direction of the lateral arm 24A. The rotating unit 24 is driven and operated under the control of the control and calculation apparatus 12.

An X-ray tube 31 and a detector 32 are respectively mounted on the tip portions of the left and right vertical arms 24B and 24C. The X-ray tube 31 is, for example, a rotary anode X-ray tube.

The detector 32 is, for example, an X-ray detecting element composed of a semiconductor material, such as cadmium telluride (CdTe). Alternatively, the detector 32 is a digital X-ray detector that uses an imaging plate. As an example, the detector 32 has an X-ray detection surface 32A (see FIG. 2) that is 6.4 mm width×150 mm height. For example, 64×1500 pixels composed of the above-described X-ray detecting elements are formed on the detection surface. As a result, incident X-rays can be collected at a frame rate of 300 fps (a single frame being, for example, 64×1500 pixels), for example, as image data in digital electric quantity based on the quantity of the X-rays. The collected data is referred to, hereafter, as "frame data".

Figure 2:
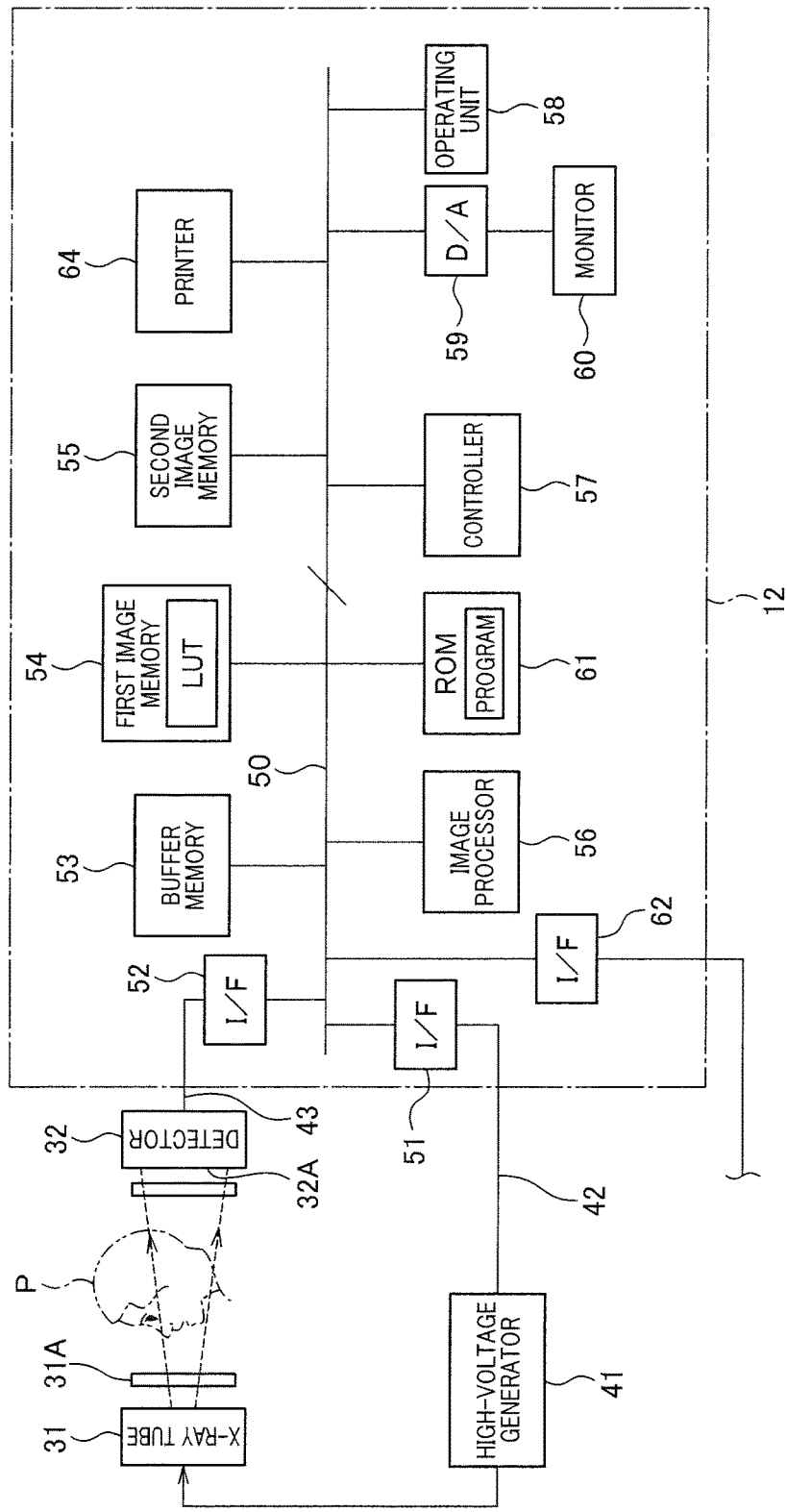
FIG. 2 is a block diagram of an example of an electrical configuration of the panoramic imaging apparatus.

FIG. 2 shows an electrical block diagram for control and processing of the panoramic imaging apparatus.

As shown in FIG. 2, the X-ray tube 31 is connected to the control and calculation apparatus 12 via a high-voltage generator 41 and a communication line 42. The detector 32 is connected to the control and calculation apparatus 12 via a communication line 43. The high-voltage generator 41 is provided in the support column portion 22, the up/down moving unit 23, or the rotating unit 24. The high-voltage generator 41 is controlled by control signals from the control and calculation apparatus 12, based on X-ray irradiation conditions, such as a tube current and a tube voltage of the X-ray tube 31, as well as an irradiation timing sequence. The X-ray tube 31 is provided with a slit 31A that restricts the field of view of the X-rays that are emitted.

The control and calculation apparatus 12 is configured by, for example, a personal computer that capable of storing a large volume of image data, because a large quantity of image data is handled, for example. That is, the control and calculation apparatus 12 includes, as main constituent elements, interfaces 51, 52, and 62, a buffer memory 53, a first image memory 54 (storage means), a second image memory 55, an image processor 56, a controller (central processing unit (CPU)) 57, and a digital-to-analog (D/A) converter 59 that are communicably connected to each other via an internal bus 50. The controller 57 is communicably connected to an operating unit 58. The D/A converter 59 is connected to a monitor 60. A printer 64 is connected to the internal bus 50.

Of the constituent elements, the interfaces 51 and 52 are respectively connected to the high-voltage generator 41 and the detector 32. The interfaces 51 and 52 mediate communication of control information and collected data exchanged between the controller 57, and the high-voltage generator 41 and the detector 32. The other interface 62 connects the internal bus 50 and a communication line, and enables the controller 57 to communicate with an external apparatus. As a result, the controller 57 is capable of loading intraoral images captured by an intraoral X-ray imaging apparatus that is present outside, and sending, to an external server, panoramic images captured by the present imaging apparatus and focus-optimized images based on the panoramic images in compliance with, for example, Digital Imaging and Communications in Medicine (DICOM) standards, as needed.

The buffer memory 53 temporarily stores therein frame data in digital quantity that is received via the interface 52 from the detector 32.

In addition, the image processor 56 is placed under the control of the controller 57. The image processor 56 has a function for interactively performing, with an operator, generation of a panoramic image of a standard tomographic plane along the dentition of a patient and processes for subsequent use of the panoramic image (including a process for examining the occurrence and state of progression of periodontal disease, described hereafter). A program for actualizing this function is stored in a read-only memory (ROM) 61 in advance.

Figure 3:
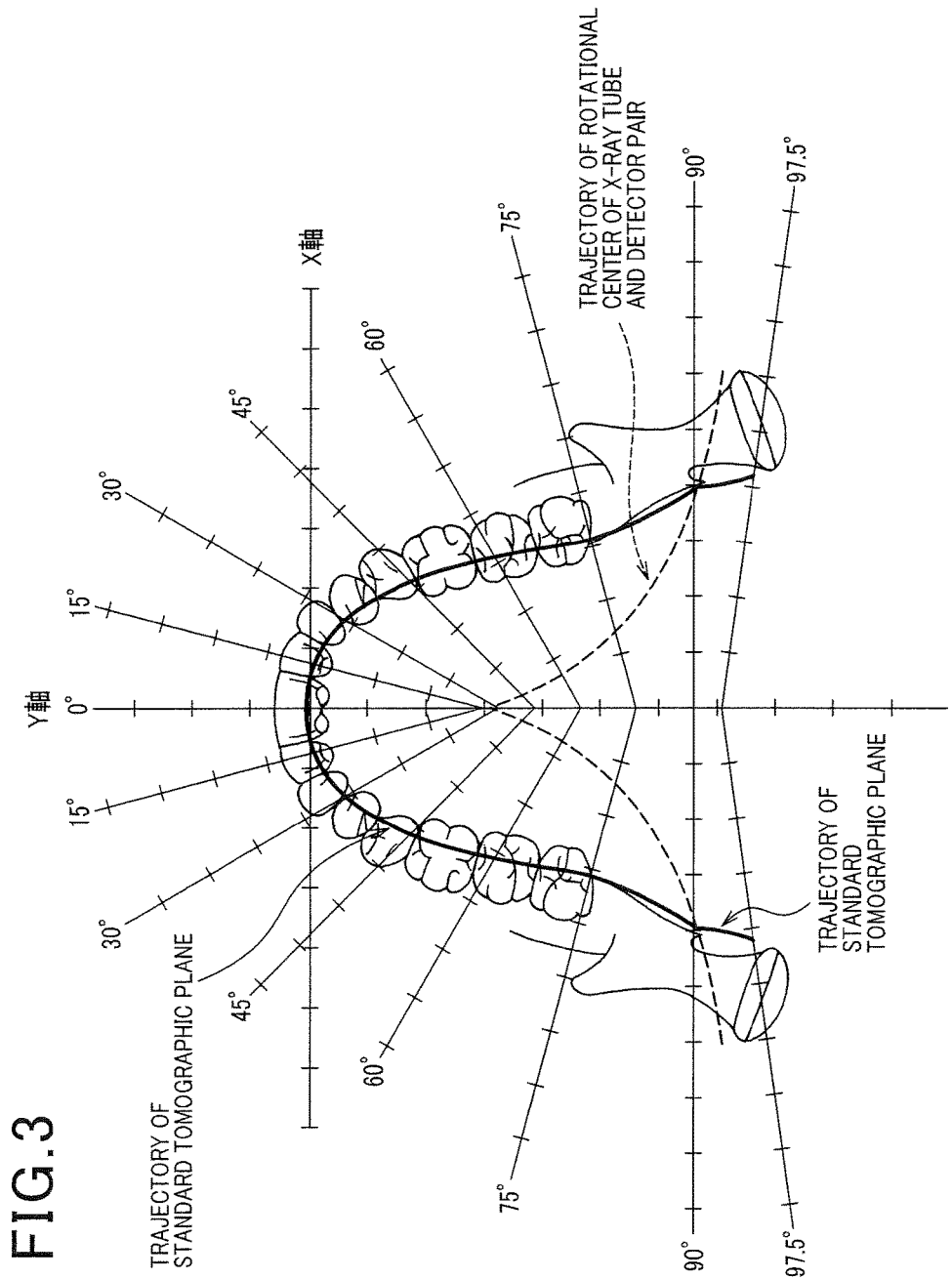
FIG. 3 is a diagram of a projection trajectory onto an XY plane of a standard tomographic plane set in a dentition.

According to the present embodiment, the standard tomographic plane is provided as a tomographic plane that is selected from standard tomographic planes of a plurality of sizes prepared in advance to be used for adults, for children, and the like. The standard to tomographic plane refers to a virtual curved tomographic plane (a tomographic plane that has a horseshoe shape when viewed from a vertical direction) that is set based on statistical data on the shape and size of dentition in humans. FIG. 3 shows an example of a selected standard tomographic plane for adults. Therefore, the teeth of a subject having the standard shape and size are arrayed with the tomographic plane at the center and along the curved plane thereof. Therefore, the panoramic image of the standard tomographic plane itself already serves as an optimally focused image. However, in actuality, each individual subject has dentition that is displaced, locally or in its entirety, from the standard tomographic plane.

Figure 4:
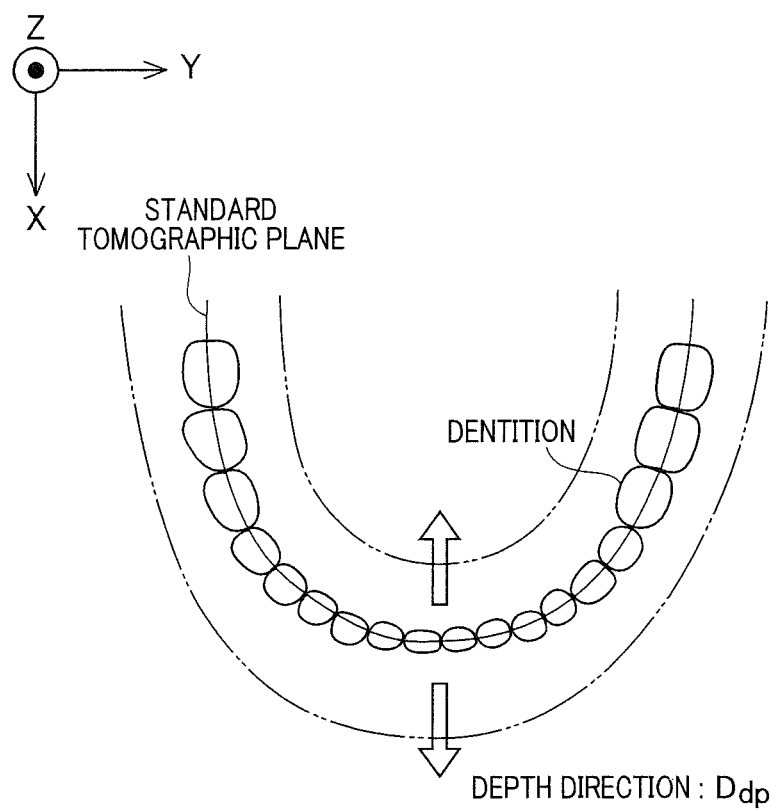
FIG. 4 is a diagram for explaining the movement, on the XY plane, of a plane from the standard tomographic plane set in the dentition.

Therefore, when a region of interest is out of focus in the panoramic image of the standard tomographic plane, which is an initial image that is first reconstructed, an image that is in optimal focus can be acquired through use of frame data that has already been collected. In other words, rescanning is not required to be performed. As described above, the panoramic imaging apparatus 1 according to the present embodiment uses the configuration described in JP-A-2007-136163. Therefore, a second reconstruction can be also achieved simply through reconstruction based on the frame data that has been initially collected and gain (described hereafter) based on a new desired cross-sectional position in an imaging space. As shown in FIG. 4, the new position may be a position at which the tomographic plane itself that is to be brought into focus is shifted by a desired distance along the depth direction of the dentition from the position of the standard tomographic plane. Alternatively, the new position may be an oblique partial tomographic plane in which the area including the region of interest is moved in the depth direction of the dentition or rotated (tilted) around an axis of the area, in the image of the standard tomographic plane.

Returning to FIG. 2, the frame data and image data to be processed or being processed by the image processor 56 are readably and writably stored in the first image memory 54. A large capacity recording medium (non-volatile, and readable and writable), such as a hard disk, is used as the first image memory 54. In addition, the second image memory 55 is used to display the generated panoramic image data and/or the post-processed panoramic image data. The image data stored in the second image memory 55 is retrieved by the D/A converter 59 at a predetermined cycle, converted to analog signals, and displayed on a screen of the monitor 60.

The controller 57 controls the overall operations of the constituent elements of the apparatus based on a program for carrying out overall control and processing that is stored in the ROM 61 in advance. The program interactively receives operation information for predetermined items from an operator. Therefore, as described hereafter, the controller 57 is capable of interactive operation, taking into consideration the setting of a parameter (referred to as gain or a shift & add quantity) required for generation of a panoramic image of a standard tomographic plane and reconstruction for carrying out focus optimization (that is, a process for reducing blurriness of an image) of the panoramic image, collection of frame data (scanning), and information on operations by an operator outputted from the operating unit 58.

Therefore, as shown in FIG. 1, the patient places his or her chin at the position of a chin rest and holds a mouthpiece 26 in his or her mount, while in a standing or sitting position. The patient also presses his or her forehead against a head rest 28. As a result, the position of the head portion (jaw portion) of the patient is fixed at substantially the center portion of a rotation space of the rotating unit 24. In this state, the rotating unit 24 rotates around the head portion of the patient along the XY plane and/or along a plane that is oblique to the XY plane (see the arrows in FIG. 1), under the control of the controller 57.

During this rotation, under the control of the controller 57, the high-voltage generator 41 supplies the X-ray tube 31 with a high voltage for irradiation (designated tube voltage and tube current) in, for example, pulse mode at a predetermined cycle. The X-ray tube 31 is thereby driven in pulse mode, for example. As a result, pulse-like X-rays are emitted from the X-ray tube 31 at a predetermined cycle. Of course, the X-ray tube 31 may be driven in continuous mode, and the X-ray may be continuously emitted.

The X-ray that is emitted in this way passes through the jaw portion (dentition portion) of the patient positioned at the imaging position, and enters an incidence surface 32A of the detector 32. As described above, the detector 32 detects the incident X-rays at an extremely high frame rate (such as 300 fps), and successively outputs the detected incident X-rays as frame data (such as 64×1500 pixels) in the corresponding electric quantity. The frame data is temporarily stored in the buffer memory 53 via the communication line 43 and via the interface 52 of the control and calculation apparatus 12. The temporarily stored frame data is subsequently transferred to and stored in the first image memory 54.

Therefore, the image processor 56 is capable of generating a panoramic image along the standard tomographic plane along the dentition through reconstruction using the frame data stored in the first image memory 54. In addition, the image processor 56 is capable of generating a focus-optimized image through reconstruction using the frame data composing a region of interest (ROI) designated in the panoramic image. The panoramic image itself is also a cross-sectional image of the overall standard tomographic plane that is generated with the intention to optimize the focus. However, in actuality, because the shape of the dentition differs among individual subjects, acquiring an image in which blurred focus is minimized (most clearly in focus within the range of capability that can be exhibited by the apparatus, or in other words, focus is optimized) in each region is difficult with the standard tomographic plane alone. Therefore, reconstruction for acquiring a cross-sectional image that more clearly shows (less blurring and more in focus) the internal structure is performed with the panoramic image of the standard tomographic plane (a cross-sectional image covering at least the overall dentition) being used as the base. This post-processing reconstruction is often performed on a partial region of the panoramic image that serves as the base. According to the present embodiment, the cross-sectional image of the partial region is also considered a focus-optimized image.

In this way, generation of a focus-optimized image that includes the panoramic image serving as the base accompanies a process referred to as reconstruction. Reconstruction is performed by a process based on the tomosynthesis method. The tomosynthesis method is publically known through, for example, the above-described JP-A-2007-136163, as well as JP-A-H04-144548 and the like. In simple terms, tomosynthesis is a process in which a plurality of pieces of frame data (two-dimensional mapping of pixel values) are shifted in relation to each other along a direction corresponding to the scanning direction, overlapped with each other, and added. The amount of overlapping is referred to as gain (or shift & add quantity) as described above. As a result of a shift-and-add process based on the gain, the pixel values of the tomographic plane at a desired position in the dentition depth direction (see FIG. 4) are emphasized. The pixel values of other tomographic planes are blurred. As a result, a panoramic image of a tomographic plane at the desired position is acquired.

The region of interest set in the panoramic image is ordinarily designated in the panoramic image as a partial region configuring a portion of the panoramic image. However, the overall panoramic image can also be set as the region of interest. Of course, a partial focus-optimized image is generated when desired by a doctor or the like.

The data of the panoramic image and/or the partial focus-optimized image is held in the first image memory 54 and displayed in the display 60 in an appropriate mode.

The capturing and reading of a panoramic image using the panoramic imaging apparatus 1 is generally as described above. According to the present embodiment, the gain used to generate the panoramic image of the standard tomographic plane (this image also being a focus-optimized image) and the partial focus-optimized image of a designated area is set in advance by calibration using phantoms, as described in above-described JP-A-2007-136-163. The gain refers to "a quantity indicating the degree of overlap", that is, the degree of positional shifting of each set of frame data during overlapping. When the gain is small, the degree of overlapping is dense. When the gain is large, the degree of overlap is rough.

Figure 5:
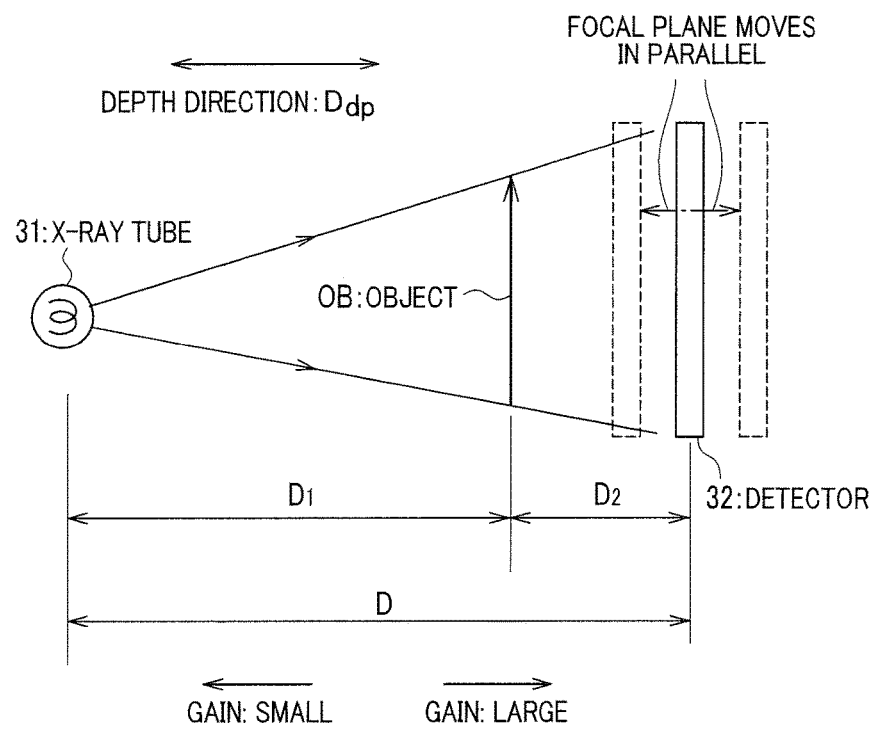
FIG. 5 is a diagram for explaining the concept of gain used in a panoramic image.

An example of the gain will be described using a simplified model in FIG. 5. In the model, distances D1 and D2 (respectively distances in the direction (depth direction) along a straight line connecting the X-ray tube and the detector at each point on the dentition) are the respective distances of the X-ray tube 31 and the detector 32 in relation to an object OB (the dentition at the jaw portion of the patient). The X-ray tube 31 and the detector 32 are moved while holding constant a relative ratio of the distances D1 and D2 and holding a relative operating speed at a certain value. In this case, an amount of overlap (gain) of the frame data (gain) at which the object OB does not become blurred (that is, the object OB is in focus) is determined.

In other words, when scanning is performed as described above, a focal plane (a continuous cross-section that is in focus) can be established based on the relative movement speed of the scanning X-ray in relation to the subject, and the gain. The focal plane corresponds to the ratio of the distances D1 and D2. Therefore, the focal plane is positioned on a plane that moves in parallel from the detector 32 in each depth direction.

In general, as the gain decreases, the focal position becomes closer to the X-ray tube 31 in each depth direction Ddp. As the gain increases, the focal position becomes farther from the X-ray tube 31 in each depth direction Ddp. Therefore, a phantom is used that quantitatively indicates the distance interval between the X-ray tube 31 and the detector 32 in the depth direction perpendicular to the dentition at each position of the dentition. Through use of the phantom, a quantitative measurement (setting) of the gain that enables focusing is performed in advance for each position on the straight line along each depth direction.

In other words, the relationship between each position (each distance from the standard plane) and the gain is measured in advance using the phantom. The relationship information is stored in the first image memory 54, for example, as a lookup table (LUT).

[Operations for the Acquisition of a Panoramic Image and Periodontal Disease Check]

Figure 6:
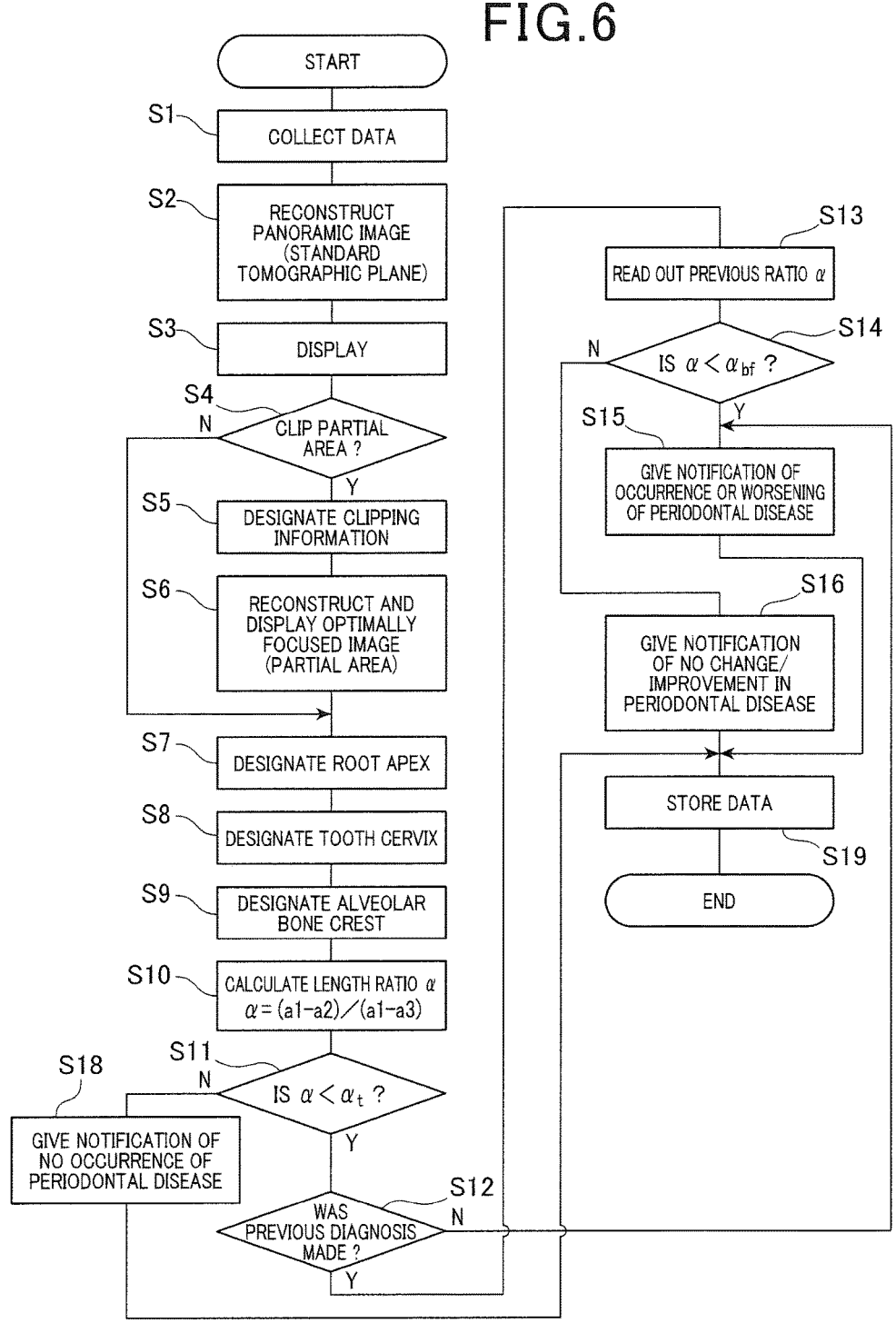
FIG. 6 is a schematic flowchart for explaining the flow of scanning, image reconstruction, and periodontal disease check performed by an image processor of the panoramic imaging apparatus according to the first embodiment.

These operations are interactively performed with the operator by the image processor 56, as shown in FIG. 6, under the control of the controller 57.

First, the operator (such as a dentist) positions the jaw portion of a patient P on the chin rest. The operator then drives the panoramic imaging apparatus 1 and collects radiolucency data of the jaw portion as frame data (FIG. 6, step S1). The series of frame data accompanying X-ray scanning is stored in the first image memory 54.

Figure 7:
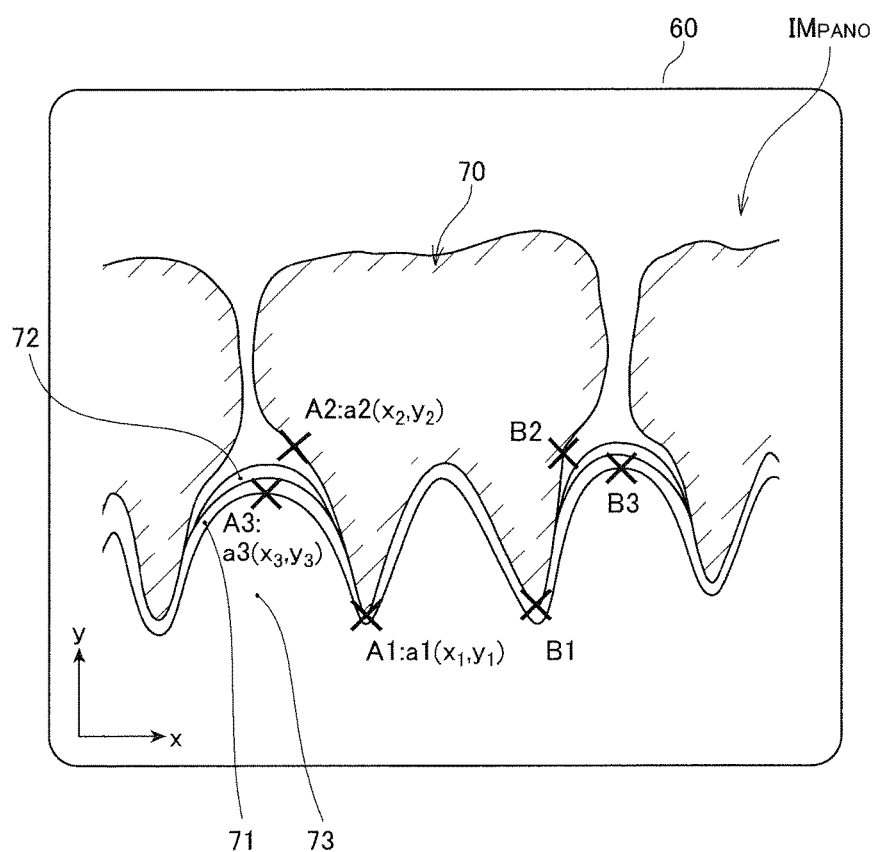
FIG. 7 is a diagram for explaining the concept of periodontal disease check according to the first embodiment.

Next, based on an instruction from the operator, the image processor 56 reads out the frame data from the first image memory 54, and reads out the gain in each depth direction corresponding to the standard tomographic plane from the lookup table LUT. The image processor 56 performs the shift-and-add process on the frame data using the gains. That is, a panoramic image $IM_{PANO}$ is reconstructed based on the tomosynthesis method. As a result, the panoramic image $IM_{PANO}$ along the standard tomographic plane in an imaging space defined between the mutually opposing X-ray tube 31 and detector 32 is generated by the X-ray tube 31 and the detector 32 being rotated (FIG. 6: step S2). FIG. 7 schematically shows a portion of the panoramic image $IM_{PANO}$.

The image processor 56 displays the panoramic image $IM_{PANO}$ of the standard tomographic plane on the monitor 60, in response to an instruction from the operator (step S3).

Next, the operator determines whether or not to clip a partial region, interactively with the image processor 56, while observing the displayed panoramic image $IM_{PANO}$ of the standard tomographic plane (step S4). The partial region is used to check the occurrence of periodontal disease or the state of progression of periodontal disease. Therefore, as the partial region, a desired portion is selected from the overall standard tomographic plane.

When determination is made that the partial region is to be clipped at step S4 (YES), next, the position and angle for clipping of the partial region are interactively designated (step S5).

In the case of a partial region along the standard tomographic plane, the designation is made by, for example, the operator setting an ROI (region of interest; such as a rectangular ROI) having a shape corresponding to the area in the panoramic image $IM_{PANO}$, and providing the position of the ROI in the depth direction of the dentition.

Even when the partial region intersects the standard tomographic plane at an angle, the designation is made by, for example, the operator designating the position of the partial region in the panoramic image $IM_{PANO}$ and providing the size (such as the size of a rectangular shape) of the partial region. In the latter case, a partial region (an area of a cross-section that passes through some teeth at an angle) that intersects the dentition at an angle at a desired position of the dentition is designated. Therefore, the latter case is suitable for checking of the occurrence of periodontal disease or the state of progression of periodontal disease.

When clipping information for the partial region is provided in this way, the image processor 56 uses the frame data that has already once been collected to reconstruct again the optimally focused image of the partial region, and displays the optimally focused image in the display 60 (see FIG. 6: step S6). In a manner similar to the reconstruction of the panoramic image of the standard tomographic plane described above, in this reconstruction as well, the gain corresponding to a position in the imaging space of the designated partial region is read out from the lookup table. The frame data is subjected to shift-and-add using the gain. As a result, a tomographic image with less blurring is acquired in which the designated partial region is optimally focused.

When the partial region for determination of periodontal disease is not to be clipped at step S4 (NO at step S4), the processes at steps S5 and S6 are skipped.

Of course, in the periodontal disease check, the panoramic image of the standard tomographic plane that is the initial image delineating the overall jaw portion may be used as is, without clipping of the partial region, as described above. However, in most cases, the localized portion on which the check for periodontal disease is performed is displaced from the standard tomographic plane, despite differences in the extent. Therefore, clipping of the partial region and optimal focusing of the partial region can be performed again, as described above, if needed.

The processes from steps S1 to S6, described above, are similar to those described in JP-A-2007-136163.

When the above-described preparation is completed, the image processor 56 starts the process for periodontal disease determination based on an instruction from the operator (steps S7 to S11).

Here, as shown in FIG. 7, the monitor 60 is presumed to currently display the optimally focused image of the partial region in the panoramic image $IM_{PANO}$ for periodontal disease check that has been reconstructed and displayed at step S6. The image is an image along the curved dentition direction.

As shown in FIG. 7, a tooth 70 is supported by the alveolar bone 73 with the periodontal membrane and the gingiva 72 therebetween.

First, based on information on an operation of the operating unit 58 by the operator, the image processor 56 designates a tip portion of the tooth root portion, that is, a root apex A1 that is the tip of the deepest root of the tooth as a feature point (reference point) of the tooth 70, using the ROI (region of interest) indicated by symbol x, in the panoramic image $IM_{PANO}$ (which is the optimally focused image of the overall dentition) along the dentition or a partial optimally focused image intersecting the dentition at an angle (step S7). In a similar manner, the image processor 56 interactively designates a tooth cervix A2 that corresponds to a constricted portion of the side surface of the tooth, positioned between the tooth root portion and the tooth crown portion in the ROI indicated by symbol x (step S8). The tooth cervix A2 is designated based on a rough idea that, in a healthy tooth, the tooth should be covered by the gingiva 72 up to this portion. The shape of the ROI is not an issue as long the position can be designated.

Next, based on information on an operation of the operating unit 58 by the operator, the image processor 56 similarly designates a crest A3 of the alveolar bone 73 in the ROI indicated by symbol x (step S9). The designations are operations that constitute a key part of the periodontal disease check. When periodontal disease has occurred or when the condition has progressed, the length (distance, depth) from the crest A3 of the alveolar bone 73 to the root apex A1 becomes short as a result of destruction or resorption of the alveolar bone 73 and the periodontal membrane 71. Therefore, the occurrence of periodontal disease can be predicted or detected, and the degree of progression thereof can be checked based on a reduction ratio of the length.

Next, the image processor 56 measures positions a1, a2, and a3 of the designated root apex A1, tooth cervix A2, and crest A3 of the alveolar bone (step S9). The position measurement is determined as position coordinates a1(x1, y1), a2(x3,y3), and a3(x2,y2) of pixel values in the image. A two-dimensional xy coordinate system for this position measurement is set in advance on the apparatus side as a display screen. The image processor 56 calculates a ratio α of the length between A1-A3, and the length between A1-A2 based on an expression $$\alpha=(a1-a3)/(a1-a2)$$

using the position coordinates (step S10). Then, the image processor 56 compares the ratio α with a predetermined threshold $\alpha_t$, and determines whether or not $\alpha<\alpha_t$ (step S11). The threshold αt is, for example, set to $\alpha_t=2/3$, and is a value that enables differentiation of whether or not periodontal disease has occurred. The threshold αt may be changed by the operator each time.

As shown in FIG. 7, a root apex B1, a tooth cervix B2, and a crest B3 of the alveolar bone can also be similarly designated on the other side of the tooth 70 in the dentition direction. An analysis similar to that described above can be performed. Therefore, the determination at step S10 may be performed on one side or comprehensively performed for both sides of a single tooth 70. Alternatively, the determination may be comprehensively performed over a plurality of teeth.

When determined YES at step S11, that is, when determined that periodontal disease has occurred, the image processor 56 determines whether or not a ratio $\alpha_{bf}$ determined at a previous diagnosis is present (step S12). In the case in which the periodontal disease check has been similarly performed in the past, the ratio $\alpha_{bf}$ at that time is stored. Therefore, the value is read out from the first image memory 54 (step S13)

Furthermore, the image processor 56 determines whether or not $\alpha<\alpha_{bf}$, with the previous ratio $\alpha_{bf}$ that has been read out (step S14). When determined that $\alpha<\alpha_{bf}$ is established, the image processor 56 displays a notification that periodontal disease has progressed on the monitor 60 (step S15). Conversely, when determined that $\alpha<\alpha_{bf}$ is not established (NO at step S14), the image processor 56 displays a notification that the state of the periodontal disease has not worsened or has improved on the monitor 60 (step S16).

When determined that there is no suspicion of periodontal disease at above-described step S14, the image processor 56 displays this fact on the monitor 60 (step S18).

When notification at the steps S15, S16, and S18 are completed, the image processor 56 proceeds to step S19. The image processor 56 stores the current check result a for periodontal disease and notification content in the first image memory 54, together with patient information, such as the name of the subject and the date and time of examination, the panoramic image data of the tooth 70 that has been checked, and the like.

As described above, in the periodontal disease check method according to the present embodiment, a tomographic image in which the overall dentition or a localized area thereof is in optimal focus can be reconstructed from frame data collected by a single scanning operation. The occurrence of periodontal disease and the state of progression thereof can be easily checked through use of the image. The information can then be provided to a dentist. The dentist can finally make a final diagnosis regarding periodontal disease, taking into consideration the information, as well as actual observations and individual differences.

In the periodontal disease check method, because the resorption of alveolar bone is taken into consideration, the occurrence of periodontal disease can be predicted with higher accuracy, compared to conventional methods. In addition, compared to the dental X-ray CT apparatus, the panoramic imaging apparatus 1 enables apparatus installation cost to be reduced and can be installed with relative ease even in typical dental clinics.

In addition, compared to the dental X-ray CT apparatus, the amount of X-ray exposure per imaging is low. Therefore, there is also an advantage in that psychological stress on the patient can be reduced.

Second Embodiment

Next, a panoramic imaging apparatus according to a second embodiment of the present invention will be described with reference to FIG. 8 to FIG. 11.

The same reference numbers are used for constituent elements according to the present embodiment and subsequent embodiments or variation examples that are identical or equivalent to those according to the first embodiment, described above. Descriptions thereof are omitted or simplified.

The panoramic imaging apparatus according to the present embodiment, as well, is provided as a modality for dental use that has the functions for acquiring a panoramic image and examining for periodontal disease, in manner similar to that described above. The hardware configuration itself of the apparatus is configured in a manner similar to that of the apparatus according to the first embodiment, described above.

Unlike the panoramic imaging apparatus according to the first embodiment, for example, the panoramic imaging apparatus performs a periodontal disease examination on the overall dentition using a panoramic image (this image also being an optimally focused image) of the overall dentition captured along a reference tomographic plane.

Figure 8:
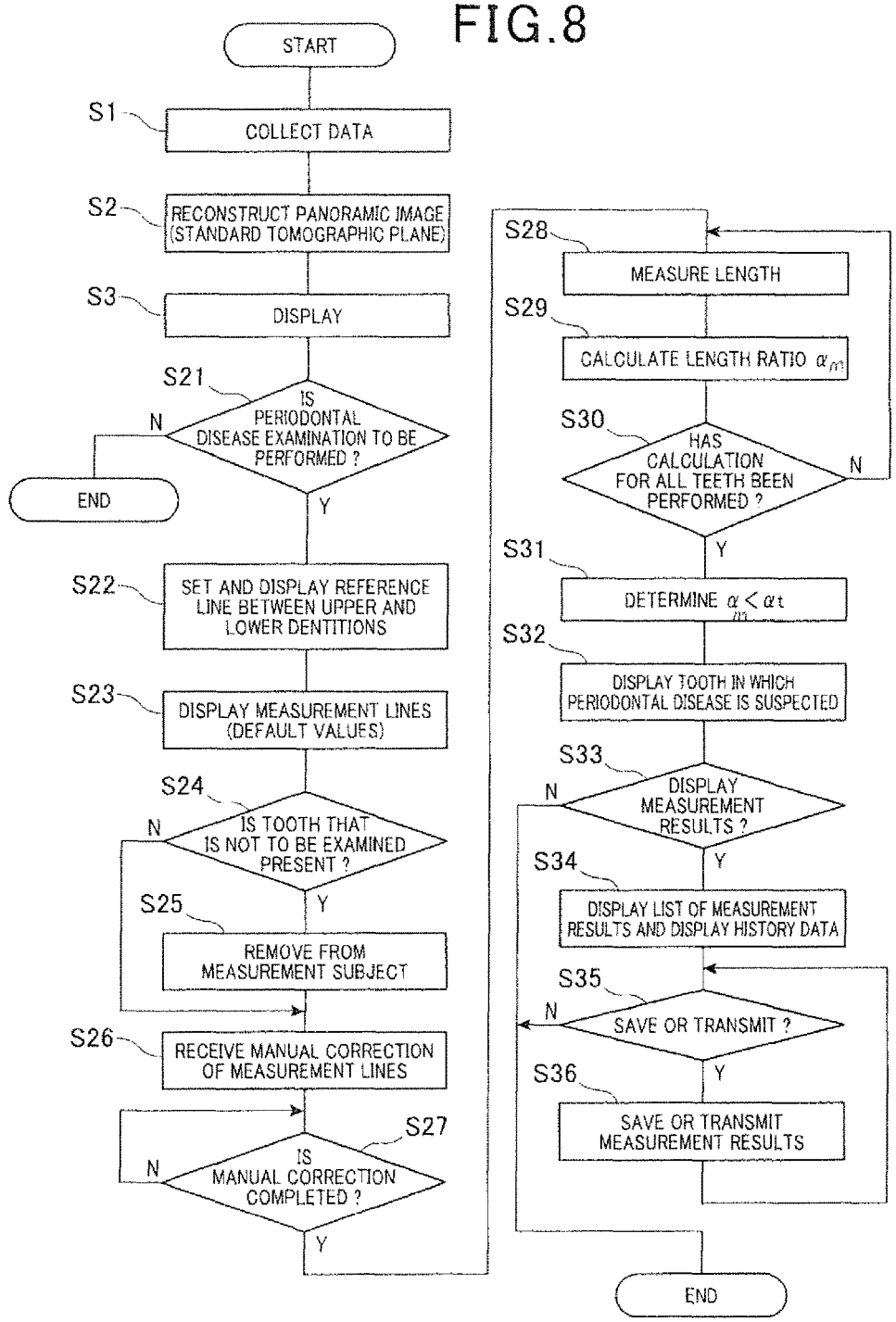
FIG. 8 is a schematic flowchart for explaining the flow of scanning, image reconstruction, and periodontal disease check performed by an image processor of the panoramic imaging apparatus according to a second embodiment.
Figure 9:
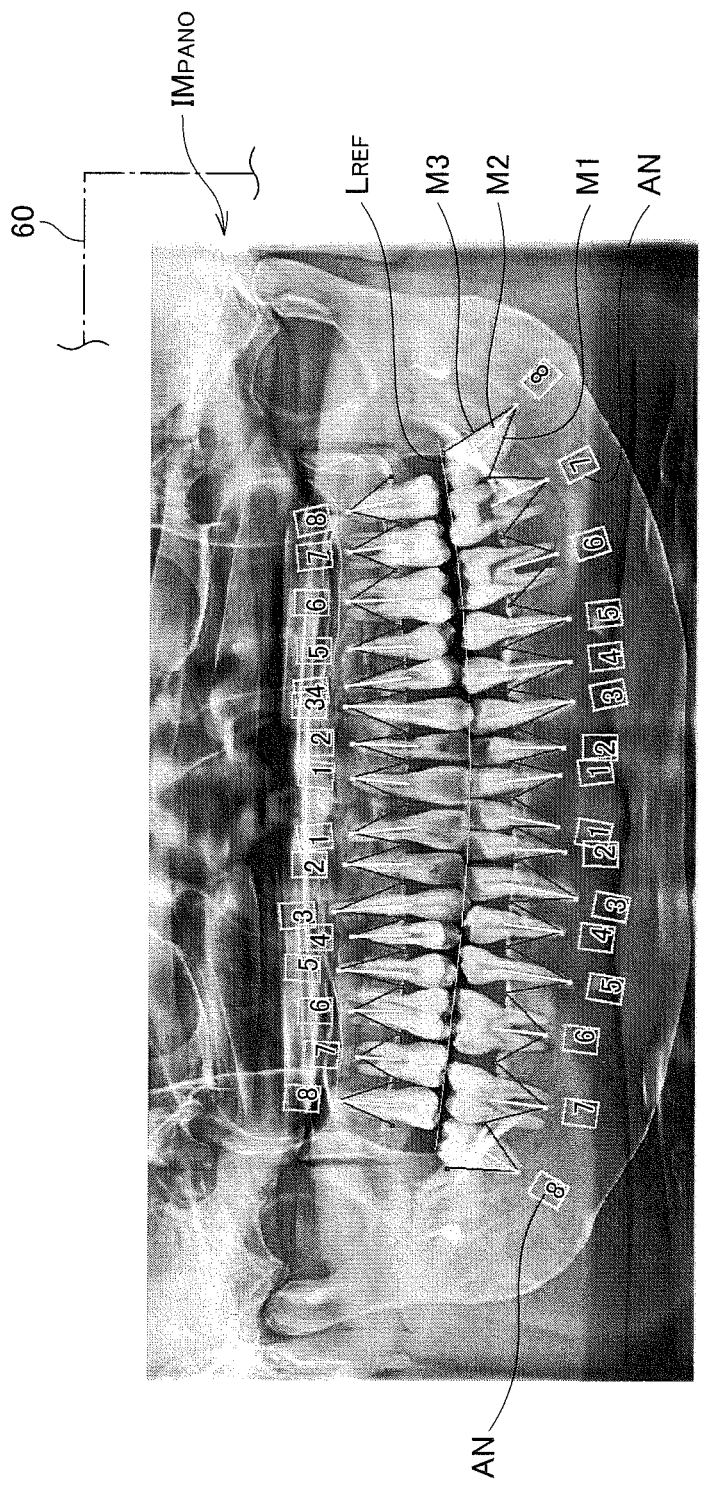
FIG. 9 is a diagram for explaining a panoramic image that is displayed and information including reference lines and measurement lines that are displayed such as to be superimposed on the panoramic image, according to the second embodiment.
Figure 10:
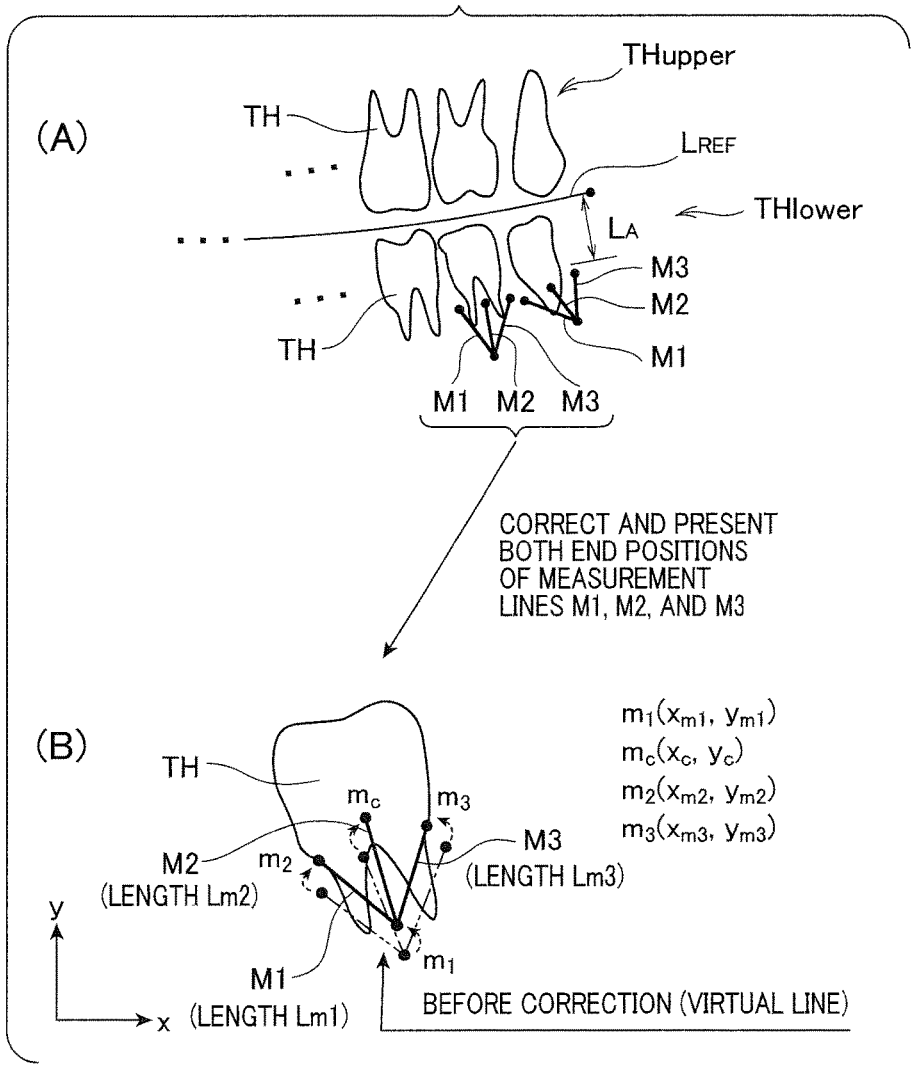
FIG. 10 is a diagram for explaining a positional relationship between the reference line and the measurement lines, and manual correction of the measurement lines.

FIG. 8 shows an overview of the periodontal disease examination that is interactively performed with an operator, with cooperation between the controller 57 and the image processor 56. In the processes in FIG. 8, steps S1 to S3 are the same as those in FIG. 6, described above. Therefore, as a result of the display process at step S3, for example, the panoramic image $IM_{PANO}$ shown in FIG. 9 is displayed on the monitor 60. In actuality, the panoramic image $IM_{PANO}$ that is initially displayed is an initial screen in which various lines and symbols shown in FIG. 9 are not displayed in a superimposing manner.

Subsequently, based on an instruction from the operator, the image processor 56 determines whether or not to perform the periodontal disease examination (step S21). When determined that the periodontal disease examination is not performed, the image processor 56 ends the process (NO at Step S21). However, when determined that the periodontal disease examination is to be performed, the image processor 56 proceeds to the processes at step S22 and subsequent steps.

First, the image processor 56, interactively with the operator, draws a reference line $L_{REF}$ between upper and lower dentitions (step S22). Whether the angle of a space forming a gap between the upper and lower dentitions is concave, convex, or substantially parallel in the panoramic image depends on the manner in which the subject draws in his or her chin. Therefore, as a result of the operator designating a plurality of points in the gap between the upper and lower dentitions in the panoramic image $IM_{PANO}$, the image processor 56 automatically draws a smooth reference line $L_{REF}$ that passes through the plurality of points and displays the reference line $L_{REF}$ on the panoramic image $IM_{PANO}$ in a superimposing manner.

Next, the image processor 56 retrieves measurement lines for each tooth based on the reference line $L_{REF}$. The measurement lines serves as default values. The image processor 56 displays, on the panoramic image $IM_{PANO}$ in a superimposing manner, the measurement lines M1, M2, and M3 separately for the upper and lower dentitions $TH_{upper}$ and $TH_{lower}$, and for each tooth TH (step S23). As schematically shown in an enlarged state in FIG. 10 (A), the measurement lines M1, M2, and M3 are stored in a state in which each is separated from the reference line $L_{REF}$ by a predetermined distance $L_A$ above or below the reference line $L_{REF}$, and adjacent to each other so as to correspond to each tooth. Therefore, at the stage at step S23 in which the measurement lines M1, M2, and M3 serving as the default values are merely displayed in a superimposing manner, unlike the state shown in FIG. 9, the measurement lines M1, M2, and M3 do not necessarily accurately indicate the desired positions on each tooth. The measurement lines M1, M2, and M3 are merely positioned near each tooth (see FIG. 10 (A)).

The measurement lines M1, M2, and M3 are prepared for each tooth, that is, for each of the 16 upper teeth and 16 lower teeth, regardless of the tooth being a front tooth or a back tooth. In the image, the measurement lines M1 and M3 on both sides are two straight lines that connect both alveolar bone crests present on both sides in the dentition direction, with the tip of the tooth root (the root apex or a center position of the tooth roots) as a reference point. In addition, the center measurement line M2 is a straight line that connects the reference point to a position (estimated position) at which the crest of the alveolar bone is estimated to be in a healthy state.

Next, the image processor 56 determines whether or not a tooth that is not to be examined or a tooth that does not require examination, and further, a portion in which a tooth is absent is present in the panoramic image $IM_{PANO}$, based on instruction information from the operator (step S24). This determination is made to address instances in which not all teeth are necessarily required to be subjected to examination. When determined YES at step S24, that is, when determined that a tooth that is not to be examined or the like is present, the image processor 56 prompts the operator to click on an annotation AN indicating the target tooth number. As a result, the image processor 56 partially deletes the measurement lines M1 to M3 corresponding to the designated annotation AN from the panoramic image $IM_{PANO}$ (step S25). When determined NO at step S24, the image processor 56 skips the process at step S25.

Furthermore, the image processor 56 receives manual correction information regarding the positions of the measurement lines M1, M2, and M3 from the operator (step S26). That is, the operator corrects the positions on both ends of the measurement lines M1, M2, and M3 for each tooth using the operating unit 58. For example, the operator performs correction by moving the points indicating the positions on both ends using a mouse. As a result, the positions on both ends of the measurement lines M1, M2, and M3 are placed in desired positions for each tooth (see FIG. 10 (B)).

Next, the image processor 56 determines whether or not position correction of the measurement lines M1, M2, and M3 for each tooth, described above, is completed (step S27). The image processor 56 performs the correction process with the operator until completion thereof. When determined that position correction of the measurement lines M1, M2, and M3 is completed YES at step S27), the image processor 56 measures the lengths of the measurement lines M1, M2, and M3 for each tooth (step S28). This measurement is performed in a manner similar to the measurement according to the first embodiment. That is, when both ends $m_1(x_{m1},y_{m1})$ and $m_c(x_c,y_c)$ of the measurement line M1, both ends $m_1(x_{m1},y_{m1})$ and $m_3(x_{m3},y_{m3})$ of the measurement line M2, and both ends $m_1(x_{m1},y_{m1})$ and $m_3(x_{m3},ym_3)$ of the measurement line M3 are taken on two-dimensional xy coordinates provided in advance on the apparatus side as a display screen, both ends of, the respective lengths Lm1 and Lm3 of the measurement lines M1 and M3 on both sides are calculated from the coordinate data of the positions on both ends thereof. Furthermore, an average value $L_{med}$ (=Lm1+Lm3)/2) of the two lengths is calculated. Still further, the length $L_2$ of the center measurement line M2 is calculated from the coordinate data of the positions on both ends thereof.

Furthermore, the image processor 56 calculates the length ratio α, described according to the first embodiment, as $$\alpha_m = L_{med}/L_2$$

(step S29). That is, as periodontal disease progresses, the position of the alveolar bone crest falls. Therefore, the value of the average length $L_{med}$ decreases. Thus, the length ratio $\alpha_m$ decreases in accompaniment with the progression of periodontal disease. Conversely, to check the degree of progression of periodontal disease, all that is required is that the manner in which the length ratio $\alpha_m$ changes in time sequence be watched.

The image processor 56 automatically repeatedly performs the calculation of the length ratio $\alpha_m$ for each tooth in the upper and lower dentitions (step S30). When the calculation for length ratio $\alpha_m$ for all teeth (may also be some of the teeth depicted in the panoramic image $IM_{PANO}$) currently being subjected to examination is completed (YES at step S30), the image processor 56 compares the length ratio $\alpha_m$ with a threshold αt prescribed in advance, and determines whether or not $\alpha_m < \alpha t$, in a manner similar to that in the above-described example (step S31). The threshold αt is, for example, set to αt=⅔, and is a value that enables differentiation of whether or not periodontal disease has occurred. The threshold αt may, of course, be changed by the operator each time.

Next, the image processor 56 displays, in color, an annotation AN indicating the number of a tooth (that is, a tooth in which periodontal disease is suspected) that satisfies a differentiation condition that is the length ratio $\alpha_m$ being $\alpha_m < \alpha_t$, in the panoramic image $IM_{PANO}$ that is currently being displayed (step S32). Of course, the value of the length ratio $\alpha_m$ may be displayed in a superimposing manner on a portion of the panoramic image $IM_{PANO}$.

Figure 11:
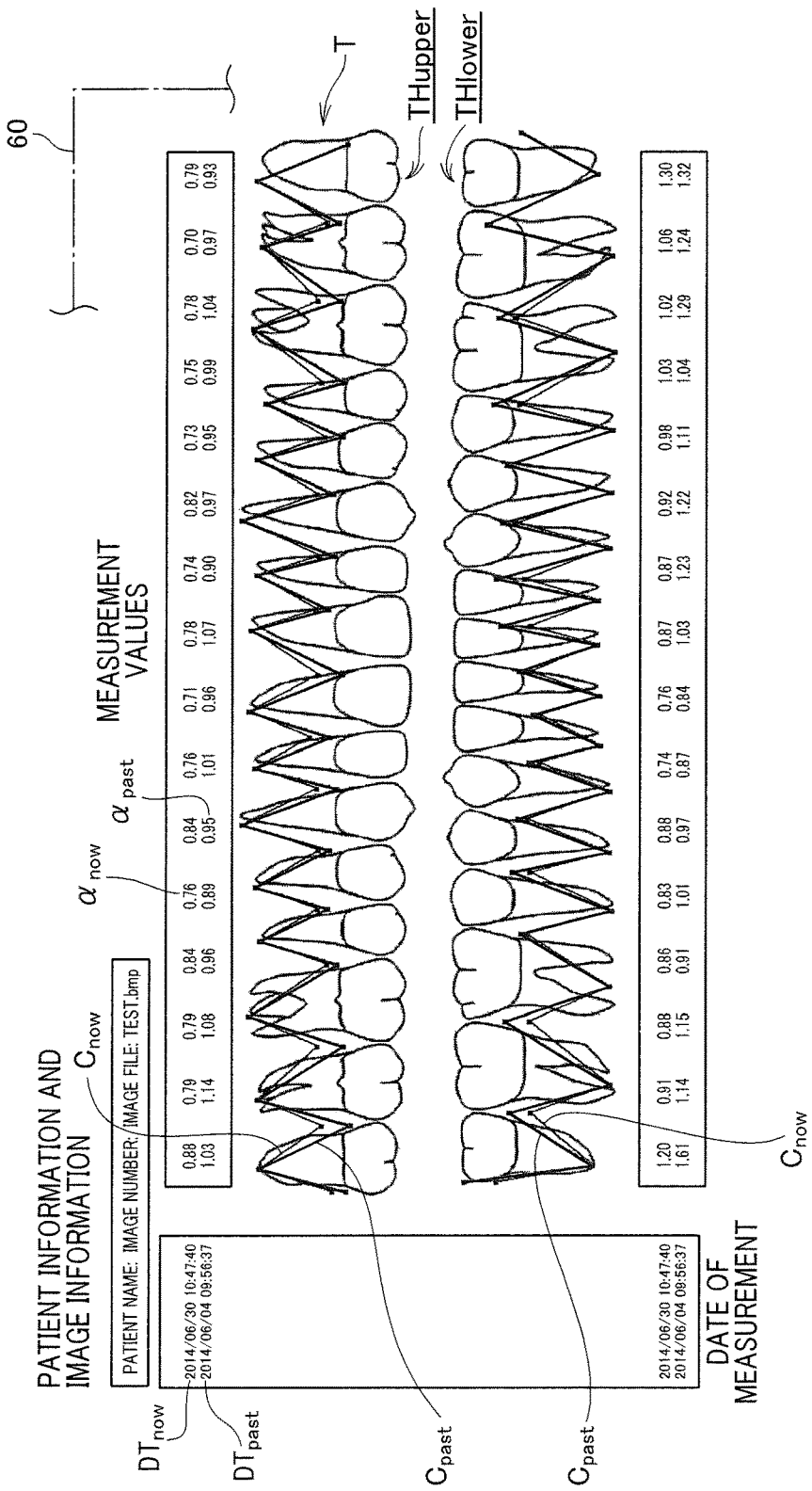
FIG. 11 is a schematic diagram of a monitor screen in which an examination for periodontal disease is displayed, according to the second embodiment.

Subsequently, as shown in FIG. 11 for example, the image processor 56 displays, in a list, the series of measurements and the results of comparison and determination, described above, on the monitor 60, together with past history data of the patient, based on a request from the operator (steps S33 and S34). In the display example, for each of the upper and lower dentitions, straight lines $C_{past}$ and $C_{now}$ that connect the alveolar bone crests are shown in accompaniment with a schematic diagram T of the dentitions of the patient. The schematic diagram may be created by a differentiation process on pixel values, from the panoramic image acquired during the initial examination. In some cases, the schematic diagram T may be a standard diagram. In short, all that is required is that changes in time sequence of the shapes indicated by the straight lines $C_{past}$ and $C_{now}$ (that is, changes in the periodontal disease) be visually understandable.

In the display example, the straight line $C_{past}$ is a line connecting the past alveolar bone crests of the patient. The straight line $C_{now}$ is that of the current examination. In the periphery of the schematic image and the straight lines, dates $DT_{past}$ and $DT_{now}$ of the past and current examinations, and further, the actual measurement ratios $\alpha_{past}$ and $\alpha_{now}$ are respectively displayed as that of the past examination and that of the current examination.

Next, the image processor 56 stores the examination results in the second image memory 55, for example, in preparation for the next examination, or transmits the examination results to an outside hospital or facility, interactively with the operator, and then ends the process (step S35 and S36).

In this way, in the panoramic imaging apparatus according to the second embodiment, in addition to the working effects achieved according to the first embodiment, the state of progression of periodontal disease can be examined with certainty over the overall dentition. The state of progression of periodontal disease can be grasped, visually and in time sequence. During the examination, the measurement lines M1 to M3 are automatically default-displayed. Therefore, the operator (dentist) is merely required to move the positions on both ends of the measurement lines M1 to M3 to the feature points of the tooth. Therefore, compared to when the feature points are designated from the start, operation labor can be significantly reduced. Furthermore, when a tooth that does not require examination is present in the panoramic image $IM_{PANO}$, the tooth can be eliminated in advance. Therefore, time required for periodontal examination can also be shortened. Furthermore, the state of progression of periodontal disease can be explained while showing the patient a monitor screen (see FIG. 11) of the panoramic image $IM_{PANO}$ and the outputted results. The patient is also able to visually understand the state of his or her own teeth.

VARIATION EXAMPLES

First and Second Variation Examples

First and second variation examples of the panoramic imaging apparatus according to the second embodiment, described above, will be described with reference to FIG. 12.

The panoramic imaging apparatus in the first and second variation examples has the same configuration as the apparatus according to the second embodiment. In addition, the panoramic imaging apparatus has a function for detecting the presence or absence of periodontal disease, or the degree of progression thereof, interactively with a user. In particular, the panoramic imaging apparatus of the first and second variation examples is characterized by the manner in which the ROI for the periodontal disease examination is set.

The images shown in FIGS. 12 (B) and (C) are partial images in which a rectangular ROI is set in a portion of the panoramic image $IM_{PANO}$ shown in FIG. 12 (A), and the localized area is enlarged. In the partial images shown in FIGS. 12 (B) and (C), the ROI for periodontal disease examination is set. Specifically, as the manner in which the ROI is set, two examples are given. In the variation examples, black circles (dots) and white circles (dots) are used as the ROI indicating the feature points or reference point of the tooth.

In the first variation example, as shown in the left-side image in FIG. 12 (B), the image processor 56 sets a set of measurement lines for a single tooth 80, interactively with the user. Based on designation information from the user, the image processor 56 designates an intermediate position C1 between two root apexes of the tooth (back tooth) 80 with a black circle in the image. The image processor 56 further respectively designates positions C2 and C3 of the tooth cervixes on both sides that are estimated to have been present in a healthy state, with white circles. In addition, the image processor 56 respectively designates positions C4 and C5 indicating the current tooth cervixes on both sides with black circles. Based on the point designation, as shown in the right-side image in FIG. 12 (B), the image processor 56 can set the measurement lines M1 and M3 respectively extending from the intermediate position C to the positions C4 and C5 of both tooth cervixes, and the measurement line M2 that extends from the intermediate position C1 to an intermediate position between the positions C2 and C3 of both tooth cervixes. Therefore, the image processor 56 may perform the processes at steps S22, and S28 to S36 in FIG. 8. As a result, the periodontal disease examination can be performed in a manner similar to that according to the second embodiment, described above. When only a single tooth root apex is present, the intermediate position C1 that serves as a reference position is set at the position of the tip thereof.

Meanwhile, in the second variation example, as shown in the left-side image in FIG. 12 (C), the image processor 56 sets two sets of measurement lines for a single tooth 80, interactively with the user. Based on designation information from the user, the image processor 56 designates respective positions C1A and C1B of two root apexes of the tooth (back tooth) 80 with black circles in the image. Next, separately for the left and right sides, the image processor 56 respective designates positions C2 and C3 of the tooth cervixes that are estimated to have been present in a healthy state, with white circles. Furthermore, the image processor 56 respectively designates positions C4 and C5 indicating the current tooth cervixes on both sides with black circles. Based on the point designation, as shown in the right-side image in FIG. 12 (C), the image processor 56 sets, respectively for both sides of the single tooth 80, measurement lines M1 and M2A that connect the position C1A on one side to the positions C2 and C4. Furthermore, the image processor 56 sets measurement lines M2B and M3 that connect the position C1B on the other side to the positions C3 and C5. Therefore, the image processor 56 may perform the processes at steps S22, and S28 to S36 in FIG. 8. As a result, the periodontal disease examination can be performed in a manner similar to that according to the second embodiment, described above. In the second variation example, the length ratio $\alpha$ of the measurement lines is respectively calculated between the measurement lines M1 and M2$a$, and between the measurement lines M2B and M3.

In this way, the feature points or reference points of the tooth can be designated by points. Based on the designated points, the above-described measurement lines can be set. Therefore, in addition to the working effects achieved according to the second embodiment, described above, an advantage is achieved in that periodontal disease examination using a partial image, in particular, is simple and convenient. In addition, when the positions (that is, the degree of bone resorption) of the alveolar bone differ between both sides in the dentition direction of the tooth, if measurement is performed on only either one of the sides, the degree of periodontal disease is determined based on approximate values. However, when measurement is performed on both sides as in the second variation example, a more accurate state of progression of periodontal disease can be grasped.

Third Variation Example

Next, a third variation example will be described with reference to FIG. 13.

The third variation example is characterized in that the above-described periodontal disease examination is performed on a dental image that is created from the panoramic image.

Figure 13:
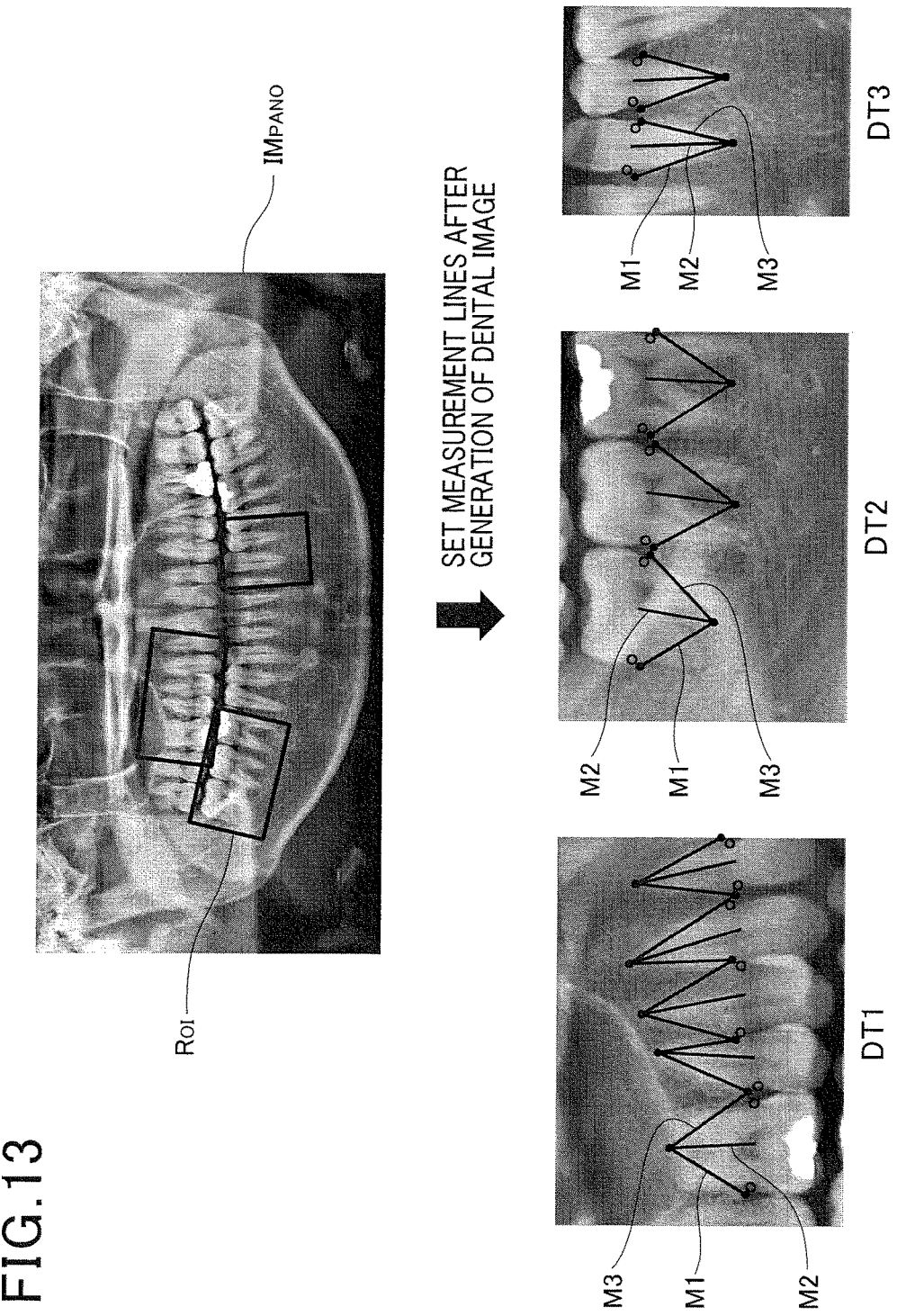
FIG. 13 is a diagram for explaining a method for setting measurement lines in a third variation example.

In the upper row in FIG. 13, the panoramic image $IM_{PANO}$ of the overall jaw portion that has been generated as described above is shown. For example, three ROI that indicate localized areas are set in the panoramic image $IM_{PANO}$. As a result, the image processor 56 can reconstruct, interactively with the operator, a perspective image along the spatial tilt of the teeth present in the localized area, by a method for generating a three-dimensional optimal focus image that is known in JP-A-2007-136163, for example. The perspective image is referred to as a dental image. The optimally focused dental image is generated through use of the frame data that had once been collected for generation of the panoramic image IMPANO. As a result, three dental images DT1, DT2, and DT3 are generated as shown in the lower row in FIG. 13, for example. The number of dental images is, of course, arbitrary.

The image processor 56 may then perform measurement based on the first variation example, described above, on one or all of the three dental images DT1, DT2, and DT3 (only the measurement lines M1, M2, and M3 are shown). Of course, measurement based on the second variation example may be performed on the dental images.

In the third variation example, in addition to the working effects based on the first and second variation examples, described above, reliability of the periodontal disease examination is further enhanced, since the dental image is a perspective image along the tilt of the teeth.

Furthermore, a blurred panoramic image may be acquired depending on positioning during imaging. However, as a result of the optimally focused dental image being used, the blurring can be resolved, and the feature points and reference points can be designated. Reliability of the periodontal disease examination can be further enhanced. As a result, reimaging is not required to be performed. The third variation example is also advantageous from the perspective of X-ray exposure.

Fourth Variation Example

Figure 14:
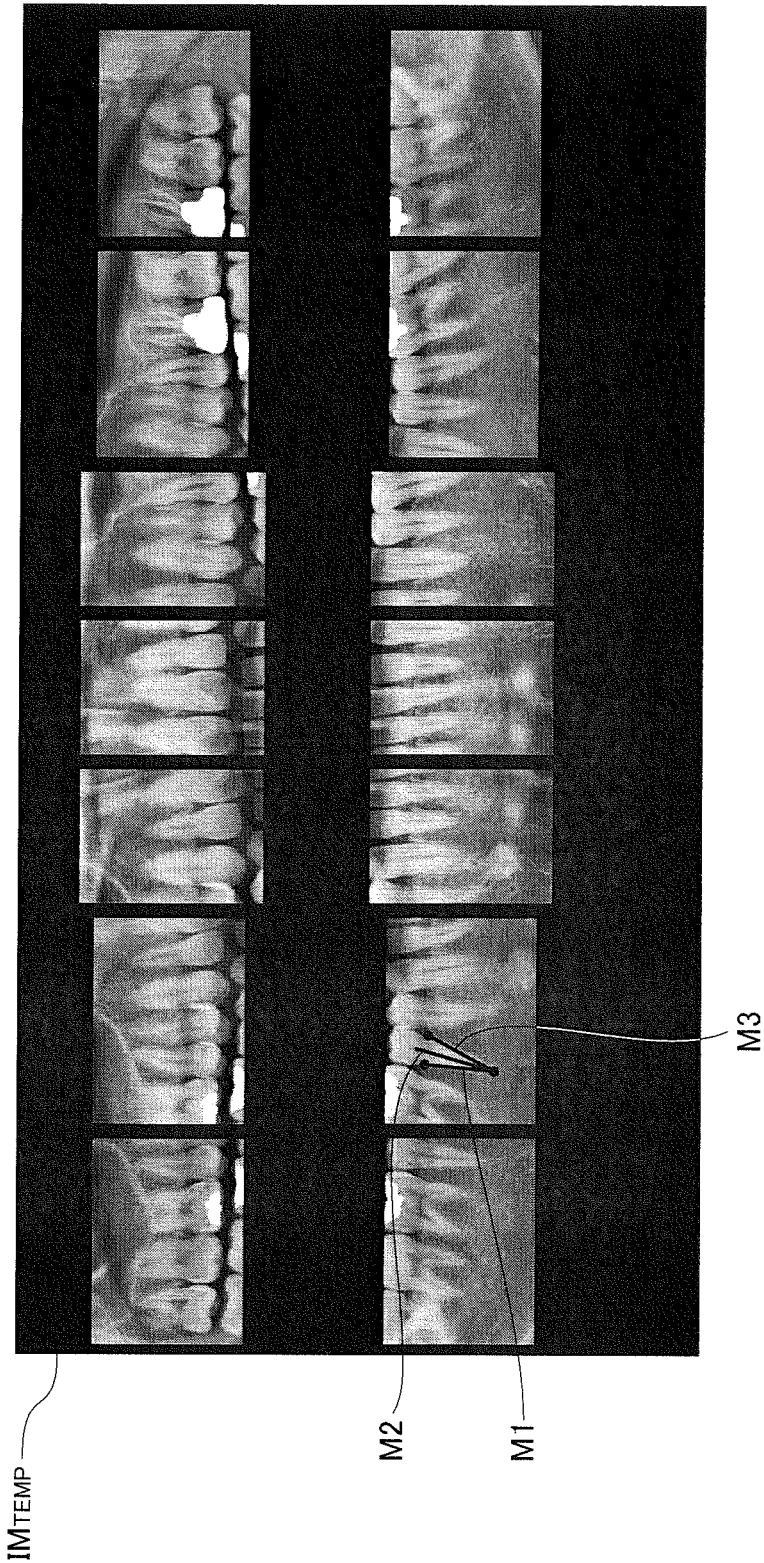
FIG. 14 is a diagram for explaining a method for setting measurement lines in a fourth variation example.

Next, a fourth variation example will be described with reference to FIG. 14.

The fourth variation example is characterized in that the above-described periodontal disease examination is performed on a template image generated from the panoramic image. In the template image, a dental image of each portion of the dentition is arrayed based on a template. In other words, dental images that are in focus are provided such as to be arrayed in a manner similar to a panoramic image.

As the template image, images in various modes are known, such as a 10-image mode, a 14-image mode, or an 18-image mode. FIG. 14 shows a template image $IM_{TEMP}$ in the 14-image mode. Measurement based on the first or second variation example, described above, may be performed using a portion of, or the entirety of, the template image $IM_{TEMP}$. In the fourth variation example as well, working effects equivalent to those of the third variation example can are achieved.

Fifth Variation Example

Figure 15:
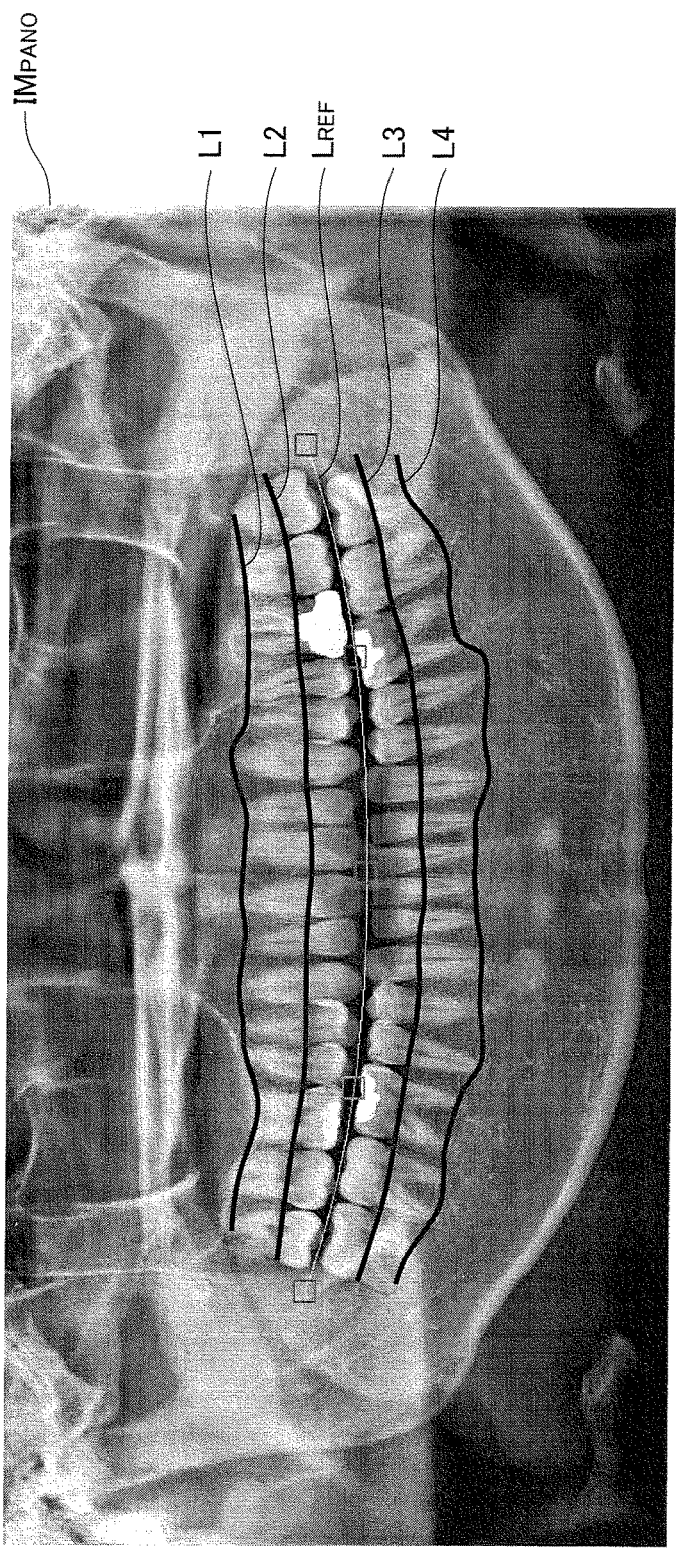
FIG. 15 is a diagram for explaining the limits in a default display of measurement lines according to a fifth variation example.

Next, a fifth variation example will be described with reference to FIG. 15 and FIG. 8.

The fifth variation example is characterized by being applicable to the second embodiment, described above, and in that a configuration is added that restricts the area of default display of the measurement lines M1, M2, and M3. Specifically, at the above-described step S22, in addition to the above-described reference line $L_{REF}$, the image processor 56 sets first restriction lines L1 and L4 that connect the bases of the tooth roots, and restriction lines L2 and L4 that connect the crests of the alveolar bone in the panoramic image $IM_{PANO}$, for each of the upper and lower dentitions $TH_{upper}$ and $TH_{lower}$. The restriction lines L1 to L4 are set by the image processor 56 receiving information on a manual operation in which the operator traces the positions of restriction lines L1 to L4 with an indicator point of a mouse, for example. As a result, five lines including the reference line $L_{REF}$ are displayed as shown in FIG. 15.

At step S23 in FIG. 8, the image processor 56 displays the above-described measurement lines M1, M2, and M3 as shown in FIG. 9, separately for above and below the reference line $L_{REF}$ and between the first restriction line L1 and the second restriction line L2 in the upper dentition $TH_{upper}$. In a similar manner, the image processor 56 displays the above-described measurement lines M1, M2, and M3 as shown in FIG. 9, between the second restriction line L3 and the first restriction line L4 in the lower dentition $TH_{lower}$ (step S23). The steps in FIG. 8 other than that described above are performed in a similar manner in the present variation example as well.

As a result, the area of default display of the measurement lines M1, M2, and M3 is restricted to the area between the first restriction line and the second restriction line, in both the upper and lower dentitions $TH_{upper}$ and $T_{lower}$. Therefore, the measurement lines M1, M2, and M3 are displayed in a superimposing manner near the tooth roots and the alveolar bone at all times. As a result, the labor involved in manual position correction of the measurement lines M1, M2, and M3, performed at steps S26 and S27 in FIG. 8 can be reduced. The working effects achieved according to the second embodiment can also naturally be achieved.

Sixth Variation Example

Next, a sixth variation example will be described with reference to FIG. 16 and FIG. 8.

The sixth variation example is also characterized by having a configuration applicable to the second embodiment, described above, and in that labor involved in setting of the measurement lines M1, M2, and M3 can be reduced.

Figure 16:
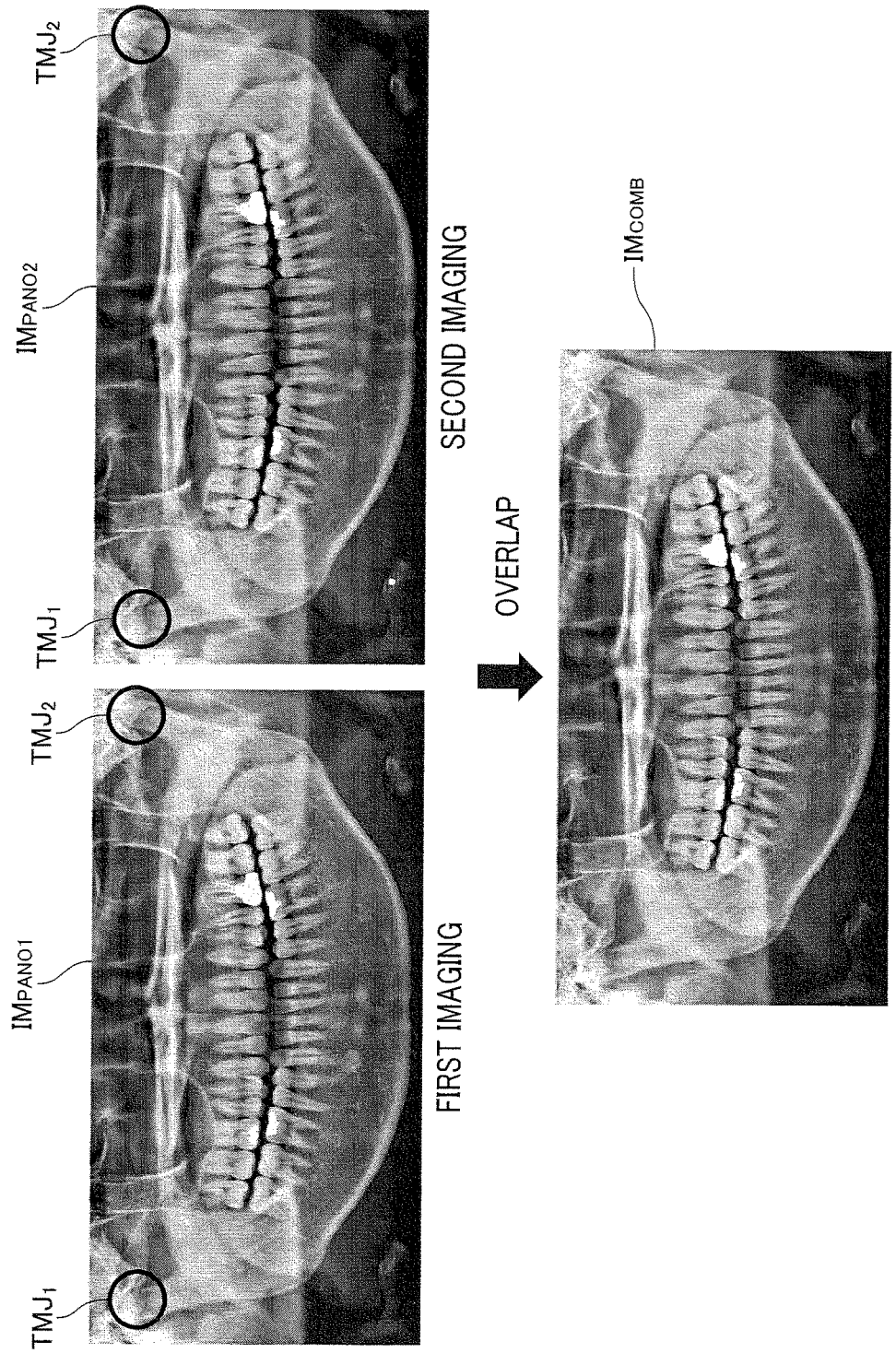
FIG. 16 is a diagram for explaining a method for setting measurement lines in a sixth variation example.

In FIG. 16, a first panoramic image $IM_{PANO1}$ and a second panoramic image $IM_{PANO2}$ that have been captured with a time lag are displayed. For example, the two images have been captured over the elapse of several months. The first panoramic image $IM_{PANO1}$ that has been captured earlier is presumed to have already been subjected to the periodontal disease examination.

In this case, the two images $IM_{PANO1}$ and $IM_{PANO2}$ are combined together in a state in which a plurality of regions that are feature points in the images, such as the left and right temporomandibular joints $TMJ_1$ and $TMJ_2$ and mental foramens (not shown), match between the images.

This may be performed by, for example, the respective density values for each pixel of the two images $IM_{PANO1}$ and $IM_{PANO2}$ being added. In this case, the first panoramic image $IM_{PANO1}$ that has been captured earlier is preferably used with reduced (lightened) pixel density. As a result, a single combined panoramic image $IM_{COMB}$ is displayed (see FIG. 16). For example, these processes may be performed by the image processor 56 during the display process at step S3 in FIG. 8.

Therefore, the combined panoramic image $IM_{COMB}$ is subsequently subjected to the processes at step S21 and subsequent steps in FIG. 8. At this time, as the display information for the reference line and the measurement lines at step S22 and S23, information that has been set in the past can be used as is. In other words, the image processor 56 may read out information on the display positions of the reference line and the measurement lines finally set in the earlier first panoramic image $IM_{PANO1}$. The image processor 56 may then use the read-out information as the setting information at the current steps S22 and S23. As a result, through use of the combined panoramic image $IM_{COMB}$ in the examination of the current second panoramic image $IM_{PANO2}$, the burden of manual operations for setting the reference line and the measurement lines can be reduced for the operator. In other words, even should there be progression in the periodontal disease, the setting positions of the reference line and the measurement lines do not change or barely change. Therefore, the past information can be used.

Furthermore, because the pixel density in the first panoramic image $IM_{PANO1}$ is reduced, when the combined panoramic image $IM_{COMB}$ is generated, a region in which periodontal disease has progressed (such as a darkened region) can be displayed in an enlarged state or the like, and changes can often be confirmed on the display screen. Such information is important to a dentist and can be used in periodontal disease diagnosis through visual observation. In addition, the measurement lines can be set in the region in a concentrated manner, thereby contributing to reduction of labor by the operator.

The algorithm for periodontal disease examination described in FIG. 6 is not necessarily required to be started as a part of the operation of the panoramic imaging apparatus 1. For example, after imaging of the panoramic image is once performed, a computer 12 may be used in a stand-alone format, for example. The computer 12 may perform the periodontal disease examination using frame data that has already been corrected. In addition, the algorithm for periodontal disease examination may be downloadable onto a remote computer by a portable recording medium or a communication means. The computer can perform a periodontal disease check in a manner similar to that described above, as long as the frame data of the patient can be acquired in some format. As a result, diagnosis of periodontal disease can be performed by a stand-alone method, even at a remote location.

Partial Reference Signs List 1 panoramic imaging apparatus
11 case
12 computer
14 imaging unit
24 rotating unit (configuring part of moving means)
31 X-ray tube (X-ray source)
32 detector
54 first image memory (storage means)
55 second image memory
56 image processor (configuring image generating means, designating means, measuring means, analyzing means, and determining means)
57 controller (configuring part of moving means)
58 operating unit (configuring parts of image generating means, designating means, and measuring means)
60 monitor (configuring parts of image displaying means, presenting means, and change information providing means)
61 ROM (configuring storage means of program for periodontal disease examination)
P patient

What is claimed is:
1. A dental panoramic imaging apparatus, comprising:
an X-ray source irradiating X-rays;
a detector receiving the X-rays, converting the X-rays to digital electric signals pixel by pixel, and outputting, as frame data, the electric signal at a constant rate;
a moving member moving the X-ray source and the detector around a jaw portion of a subject being examined, the X-ray source and the detector being located opposite to each other with the subject therebetween;
a data storage unit storing therein the frame data outputted from the detector while the moving member moves the X-ray source and the detector around the jaw portion of the subject;
a display unit;
a processor; and
an operating unit operated by a user;
wherein the processor is configured to, responsively to user's instructions issued via the operating unit,
generate data of an optimally focused panoramic image of a section along curved dentitions in the jaw portion, based on the frame data stored in the data storage unit;
display the generated optically focused panoramic image on the display unit;
superimposedly display both information and a measurement line on the panoramic image displayed on the display unit, the information indicating a restricted range in a vertical direction on the panoramic image, the vertical direction being approximately vertical to a lateral direction which is along the dentitions, the measurement line positioned within the restricted range on the panoramic image in the vertical direction, wherein said measurement line is provided for analyzing a degree of loss of alveolar bone supporting teeth at a tooth row of the jaw portion of the subject;
designate; on the panoramic image, via interactive operator input on the input unit, a position of the measurement line by changing a position of the measurement line superimposed on the panoramic image within the restricted range in the vertical direction, such that the position of the measurement line is decided based on a feature point or a reference point associated with the feature point, the feature point indicating features of both one or more teeth being targeted among the whole teeth and a support portion which supports the one or more of the whole teeth at the alveolar bone;

measure a length on the panoramic image displayed on the display unit, wherein the length is decided based on the feature point or the reference point designated; and analyze the degree of loss of the support portion of the alveolar bone, based on the measured length.

2. The dental panoramic imaging apparatus of claim 1, wherein the processer is configured to: draw, interactively with the user via the input device, a reference line on the panoramic image between upper and lower dentitions composing the dentition along the lateral direction, and superimposedly display the drawn reference line on the panoramic image;

superimposedly display, on the panoramic image, the measurement line which is movable to a default position, the default position being set within the restricted range on the panoramic image in the vertical direction; and connect the position of the measurement line interactively with the operator to designate the feature point or the reference point on the panoramic image.

3. The dental panoramic imaging apparatus of claim 2, wherein
the information indicating the restricted range is a line depicted along each of upper and lower dentitions of the tooth row, and
the features are a tooth cervix and a root apex of the teeth, and a crest of the alveolar bone.

4. The dental panoramic imaging apparatus of claim 2, wherein
the processor is configured to generate the data corresponding to a panoramic image of, as the section, a section along the lateral direction.

5. The dental panoramic imaging apparatus of claim 4, wherein
the processor is provided to measure
position information indicating positions of the root apex, the crest of the alveolar bone, and the tooth cervix on the panoramic image on either one or both sides of the teeth in the lateral direction; and
calculate a ratio of lengths based on an expression of (A1−A2)/(A1−A3) on either one or both sides of the teeth in the lateral direction, wherein amounts of the position information indicating the root apex, the crest of the alveolar bone, and the tooth cervix, which is measured on the panoramic image, is defined as A1, A2 and A3 respectively, and
determine whether or not the ratio of the lengths is less than or equal to a predetermined value on either one or both sides of teeth in the lateral direction.

6. The dental panoramic imaging apparatus of claim 2, wherein the processor is configured to present, to the user via the display unit, the analyzed degree of loss of the support portion of the alveolar bone.

7. The dental panoramic imaging apparatus of claim 5, wherein the processor is configured to present, to the user via the display unit, a determined result at the determination.

8. The dental panoramic imaging apparatus of claim 2, wherein
the processor is configured to generate both a panoramic image focused on a standard tomographic plane set previously along the dentition, and a partial panoramic image focused on a partial region existing at a designated potion in an imaging space and having a size arbitrarily designated on the panoramic image focused on a standard tomographic plane, the X-rays being scanned in the imaging space.

9. The dental panoramic imaging apparatus of claim 2, wherein the processor is configured to produce, into information showing temporal changes, the degree of loss of the alveolar bone analyzed by the analyzing means at each of a plurality of times based on a plurality of the frame data acquired at each of the plurality of times and stored in the storage, the plurality of times being different in time from each other.

10. The dental panoramic imaging apparatus of claim 2, wherein the processor is configured to superimposedly display, on the panoramic image, the measurement line on each of all teeth composing each of the upper and lower dentitions.

11. The dental panoramic imaging apparatus of claim 10, wherein the processor is configured to partially delete, of measurement lines displayed on all the teeth, the measurement lines displayed on a tooth which is unnecessary to perform a periodontal disease examination.

12. The dental panoramic imaging apparatus of claim 2, wherein the measurement line is composed of a pair of straight lines (M1, M3) and another single straight line (M2),
the pair of straight lines consisting of two straight lines, each of the two straight lines connecting a single reference point and a corresponding one of two crests of two alveolar bones on the panoramic image, the two crests being located on both sides of the reference point in the lateral direction on the panoramic image, the single reference point being a tip of a tooth root of the tooth,
the another single straight line connecting the reference point and a position at which the crest of the alveolar bone is estimated to be in a healthy state.

13. The dental panoramic imaging apparatus of claim 2, wherein the restricted range is provided by two sets of restriction lines, one set of the restriction lines consisting of first and second restriction lines (L1, L2) superimposed on the upper dentition and located positionally differentiated in the vertical direction, the other set of the restriction lines also consisting of first and second restriction lines (L4, L3) superimposed on the lower dentition and located positionally differentiated in the vertical direction, the measurement lines being allowed to be movable in a vertical range restricted by the first and second restriction lines of the one set of the restriction lines on the upper dentition and allowed to be movable in a vertical range restricted by the first and second restriction lines of the other set of the restriction lines on the lower dentition.

14. The dental panoramic imaging apparatus of claim 13, wherein the processor is configured to superimposedly display on the panoramic image such that i) the first restriction lines (L1, L4) of the two set of the restriction lines are superposed to mutually connect bases of the tooth roots of the teeth on the upper and lower dentitions, respectively, in the lateral direction, and ii) the second restriction lines (L2, L3) of the two set of the restriction lines are superposed to mutually connect crests of the alveolar bone on the upper and lower dentitions, respectively, in the lateral direction.

15. A dental diagnostic imaging method practiced in a dental panoramic imaging apparatus, wherein the apparatus comprises:
an X-ray source irradiating X-rays;
a detector receiving the X-rays, converting the X-rays to digital electric signals pixel by pixel, and outputting, as frame data, the electric signal at a constant rate;

a moving member moving the X-ray source and the detector around a jaw portion of a subject being examined, the X-ray source and the detector being located opposite to each other with the subject therebetween;

a data storage unit storing therein the frame data outputted from the detector while the moving member moves the X-ray source and the detector around the jaw portion of the subject;

a display unit;

a processor; and an operating unit operated by a user;

the method comprising steps, functionally provided by the processor responsively to user's instructions issued via the operating unit, the steps being:

generating data of an optimally focused panoramic image of a section along dentitions in the jaw portion, based on the frame data stored in the data storage unit;

displaying the generated optically focused panoramic image on the display unit;

superimposedly displaying both information and a measurement line on the panoramic image displayed on the display unit, the information indicating a restricted range in a vertical direction on the panoramic image, the vertical direction being approximately vertical to a lateral direction which is along the dentitions, the measurement line positioned within the restricted range on the panoramic image in the vertical direction, wherein said measurement line is provided for analyzing a degree of loss of alveolar bone supporting teeth at a tooth row of the jaw portion of the subject;

designate; on the panoramic image, via interactive operator input on the input unit, a position of the measurement line by changing a position of the measurement line superimposed on the panoramic image within the restricted range in the vertical direction, such that the position of the measurement line is decided based on a feature point or a reference point associated with the feature point, the feature point indicating features of both one or more teeth being targeted among the whole teeth and a support portion which supports the one or more of the whole teeth at the alveolar bone;

measuring a length on the panoramic image displayed on the display unit, wherein the length is decided based on the feature point or the reference point designated; and analyzing the degree of loss of the support portion of the alveolar bone, based on the measured length.

* * * * *